(12) United States Patent
Chemmalil

(10) Patent No.: US 11,275,090 B2
(45) Date of Patent: Mar. 15, 2022

(54) QUANTITATION OF GLYCAN MOIETY IN RECOMBINANT GLYCOPROTEINS

(71) Applicant: AMGEN INC., Thousand Oaks, CA (US)

(72) Inventor: Letha Chemmalil, Devens, MA (US)

(73) Assignee: Amgen Inc., Thousand Oaks, CA (US)

( * ) Notice: Subject to any disclaimer, the term of this patent is extended or adjusted under 35 U.S.C. 154(b) by 591 days.

(21) Appl. No.: 15/525,794

(22) PCT Filed: Nov. 19, 2015

(86) PCT No.: PCT/US2015/061684
§ 371 (c)(1),
(2) Date: May 10, 2017

(87) PCT Pub. No.: WO2016/081770
PCT Pub. Date: May 26, 2016

(65) Prior Publication Data
US 2018/0321252 A1    Nov. 8, 2018

Related U.S. Application Data

(60) Provisional application No. 62/082,014, filed on Nov. 19, 2014.

(51) Int. Cl.
| | | |
|---|---|---|
| *G01N 33/68* | (2006.01) | |
| *G01N 33/66* | (2006.01) | |
| *G01N 30/74* | (2006.01) | |
| *C12Q 1/34* | (2006.01) | |
| *G01N 30/88* | (2006.01) | |

(52) U.S. Cl.
CPC .......... *G01N 33/6842* (2013.01); *C12Q 1/34* (2013.01); *G01N 30/74* (2013.01); *G01N 33/66* (2013.01); *G01N 33/6854* (2013.01); *G01N 2030/8831* (2013.01); *G01N 2333/924* (2013.01); *G01N 2400/00* (2013.01)

(58) Field of Classification Search
None
See application file for complete search history.

(56) References Cited

U.S. PATENT DOCUMENTS

| | | | |
|---|---|---|---|
| 4,695,623 A | 9/1987 | Stabinsky | |
| 4,897,471 A | 1/1990 | Stabinsky | |
| 4,968,607 A | 11/1990 | Dower et al. | |
| 5,075,222 A | 12/1991 | Hannum et al. | |
| 5,149,792 A | 9/1992 | Thomason | |
| 5,272,064 A | 12/1993 | Thomason | |
| 5,395,760 A | 3/1995 | Smith et al. | |
| 5,610,279 A | 3/1997 | Brockhaus et al. | |
| 5,767,064 A | 6/1998 | Sims et al. | |
| 5,856,296 A | 1/1999 | Mosley et al. | |
| 5,981,713 A | 11/1999 | Colotta et al. | |
| 6,015,938 A | 1/2000 | Boyle et al. | |
| 6,096,728 A | 8/2000 | Collins et al. | |
| 6,204,363 B1 | 3/2001 | Zsebo et al. | |
| 6,235,883 B1 | 5/2001 | Jakobovits et al. | |
| 6,271,349 B1 | 8/2001 | Dougall et al. | |
| 6,337,072 B1 | 1/2002 | Ford et al. | |
| 2006/0238744 A1 | 10/2006 | O'Donohue et al. | |
| 2011/0121093 A1 | 5/2011 | Jarrell | |
| 2013/0269424 A1 | 10/2013 | Jarrell | |
| 2014/0178912 A1* | 6/2014 | Liu .................... | B01D 15/3847 435/18 |

FOREIGN PATENT DOCUMENTS

| | | |
|---|---|---|
| AU | 588819 A | 3/1998 |
| EP | 0 367 566 B1 | 5/1990 |
| EP | 0 460 846 B1 | 2/2002 |
| JP | 2011116692 A | 6/2011 |
| JP | 2012511722 A | 5/2012 |
| JP | 2012515922 A | 7/2012 |
| JP | 2014510267 A | 4/2014 |
| WO | 94/28391 A1 | 12/1994 |
| WO | 97/01633 A1 | 1/1997 |
| WO | 01/36637 A1 | 5/2001 |
| WO | 2010/071824 A2 | 6/2010 |
| WO | 2010068272 | 6/2010 |
| WO | 2010085251 A1 | 7/2010 |
| WO | 2012/107572 A1 | 8/2012 |
| WO | 2013/130604 A1 | 9/2013 |
| WO | 2013/155324 A1 | 10/2013 |
| WO | 2014/072503 A1 | 5/2014 |

OTHER PUBLICATIONS

Dixon, Bioanalysis, vol. 1 (8) 1389-1392 (2009). (Year: 2009).*
Karlsson, Göran, Stefan Winge, and Helena Sandberg. "Separation of monosaccharides by hydrophilic interaction chromatography with evaporative light scattering detection." Journal of Chromatography A 1092.2 (2005): 246-249. (Year: 2005).*
Nováková, Lucie, Lucie Havlíková, and Hana Vičková. "Hydrophilic interaction chromatography of polar and ionzable compounds by UHPLC." TrAC Trends in Analytical Chemistry 63 (2014): 55-64. (Year: 2014).*
Uçaktürk, Ebru. "Analysis of glycoforms on the glycosylation site and the glycans in monoclonal antibody biopharmaceuticals." Journal of separation science 35.3 (2012): 341-350. (Year: 2012).*
Jandera, Pavel. "Stationary and mobile phases in hydrophilic interaction chromatography: a review." Analytica chimica acta 692.1-2 (2011): 1-25. (Year: 2011).*
Alpert, Andrew J., et al. "Hydrophilic-interaction chromatography of complex carbohydrates." Journal of chromatography A 676.1 (1994): 191-202. (Year: 1994).*
Byrne, B., Donohoe, G., & O'Kennedy, R. (2007); Drug Discovery Today 12(7/8): 319-326.
Calhoun, A.R., King, A.D. (2007); Journal of Colloid and Interface Science 309 (2): 505-510.

(Continued)

*Primary Examiner* — Robert J Yamasaki
(74) *Attorney, Agent, or Firm* — Nathan A. Machin

(57) ABSTRACT

The invention relates to a method of determining glycan moiety on a recombinant glycoprotein using condensation nucleation light scattering detection.

15 Claims, 11 Drawing Sheets

(56) References Cited

OTHER PUBLICATIONS

Chemmalil et al., "A Novel Approach for Quantitation of Nonderivatized Sialic Acid in Protein Therapeutics Using Hydrophilic Interaction Chromatographic Separation and Nano Quantity Analyte Detection", Journal of Pharmaceutical Sciences, vol. 104, No. 1, Dec. 16, 20114, pp. 15-24, XP055242137, Washington, US ISSN: 0022-3549, DOI: 10.002/jps.24093.

Cintron, J & Risley, D. (2013); Journal of Pharmaceutical and Biomedical Analysis 78-79:14-18.

Do and Chen-Kiang (2002), *Cytokine Growth Factor Rev.* 13(1): 19-25.

Duy, S., Besteiro, S., Berry, L., Perigaud, C., Bressolle, F., Vial, H.J., Lefebvre-Tournier, I. (2012). A quantitative liquid chromatography tandem mass spectrometry method for metabolomic analysis of Plasmodium falciparum lipid related metabolites. Analytica Chemica Acta 739(20): 47-55.

Ganesa et al., "Sialylation levels influence oligosaccharide quantitation: analyzing response variability using high-pH anion-exchange chromatography and pulsed amperometric detection", Biopharm International, Advanstar Communications, Duluth, MN, US, vol. 16, No. 6, Jan. 1, 2003, ISSN: 1542-166X Abstract.

Bille and Crowshaw, 2008, Chromatography Today v.1(3), p. 26.

*Growth Factors: A Practical Approach*, McKay and Leigh, eds., Oxford University Press Inc., New York, 1993.

Hildenbrandt, G., & Aronson, N. (1979); Uptake of Asialo-glycophorin By the Perfused Rat Liver and Isolated Hepatocytes, Biochemica Et Biophysica Acta 587(3): 373-80.

Horwitz, W. (1982). Evaluation of Analytical Methods Used for Regulation of Foods and Drugs. Analytical Chemistry 54 (1): 67-76.

Hutchinson JP; Li J; Farrell W; Groeber E; Szucs R; Dicinoski G & Haddad PR. (2011); Journal of Chromatography 1281(12): 1646-55.

Ikegami, T., Tomomatsu, K., Takubo, H., Horie, K., Tanaka, N. (2008). Separation efficiencies in hydrophilic interaction chromatography. J. Chromatography 1184(1-2): 474-503.

Isakau, H., Robert, M., & Shingel, K. (2009); Journal of Pharmaceutical and Biomedical 49(3): 594-600.

Kimball, B., Arjo, W., Johnston, J. (2004); Journal of Liquid Chromatography & Related Technologies 27(12): 1835-1848.

Lin, S.L., Inoue, S., & Inoue, Y. (2000). Acid-base properties of the reaction product of sialic acid with flurogenic reagent, 1-2-diamino-4,5-methylethylene dioxybenzene (DMB) Carbohydrate Research 329(2): 447-451.

Maisonpierre et al. (1997), *Science* 277(5322): 55-60.

Mori, M., Taoda, H., Itabashi, H., Ikedo, M., & Tanaka, K. (2006), Acta Chromatographica 1 (16): 28-37.

Rüegg and Pytela (1995), *Gene* 160:257-62.

Olsovská J; Kamenik Z; Cajthaml T. (2009); Journal of Chromatography 1261(30): 5774-8.

Remsburg, J. W. (2007); (Order No. 1447279, The University of Texas at Arlington). ProQuest Dissertations and Theses 77.

Sharma, V.K., Glick, J., Vouros, P. (2012); Journal of Chromatography A 1245 (6): 65-74.

Siskos, PA. & Spyridk, MH. (1999). Determination of sialic acids in biological fluids using reversed-phase ion-pair high-performance liquid chromatography. J. Chromatogr B Biomed Sci Appl 724(2): 205-12.

Zauner, G., Deelder, M., & Wuhrer, M. (2011). A recent advance in hydrophilic interaction liquid chromatography (HILIC) for structural glycomics. Electrophoresis. 32(24): 3456-3466.

International Search Report and Written Opinion for PCT/US2015/061684 dated Jan. 29, 2016.

\* cited by examiner

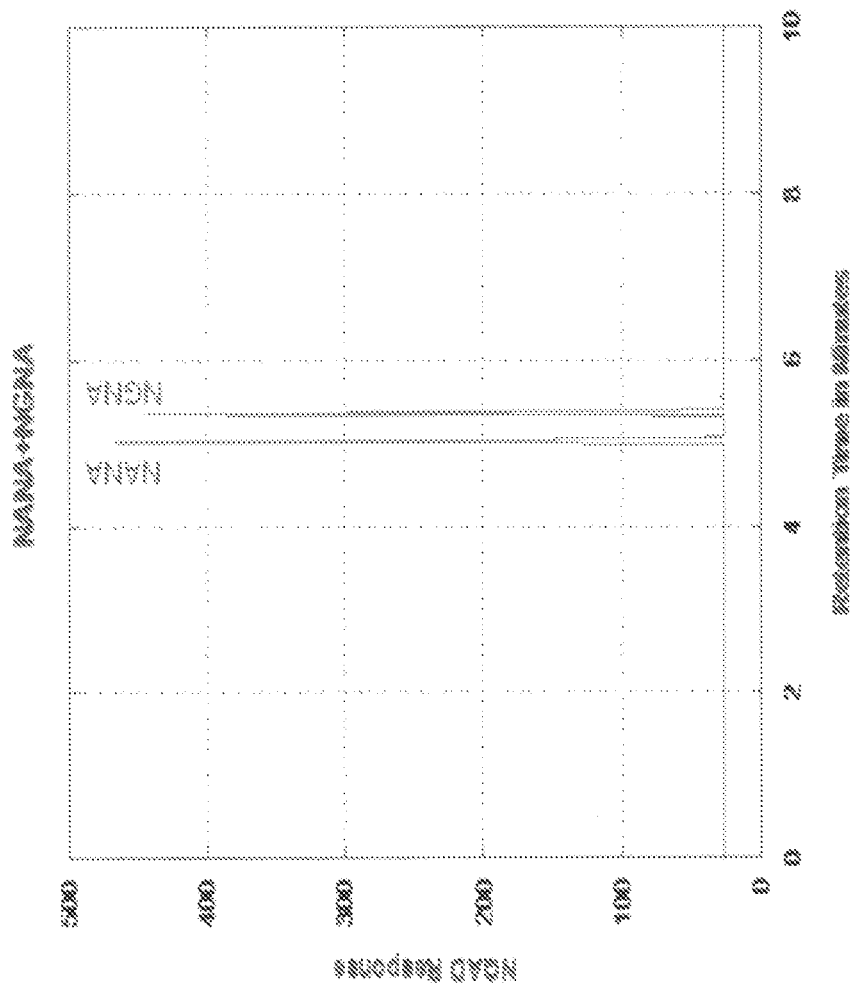
FIG. 1: Separation of NANA & NGNA on PolyGLYCOPLEX amide column (Triethyl amine/Acetonitrile under isocratic gradient condition)

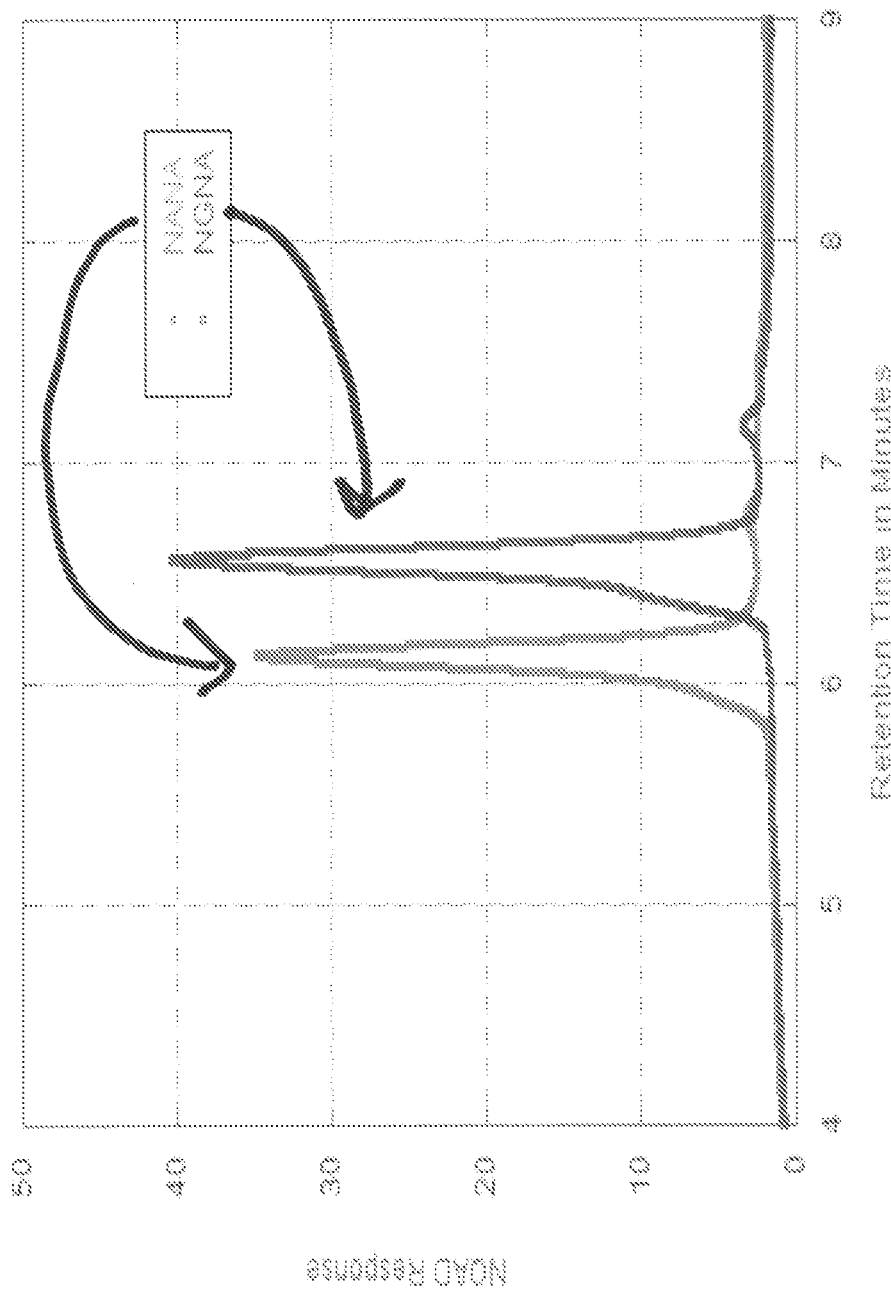
FIG. 2a: Chromatogram of NANA/NGNA on 10 cm PolyGLYCOPLEX amide column using 20% Formic Acid

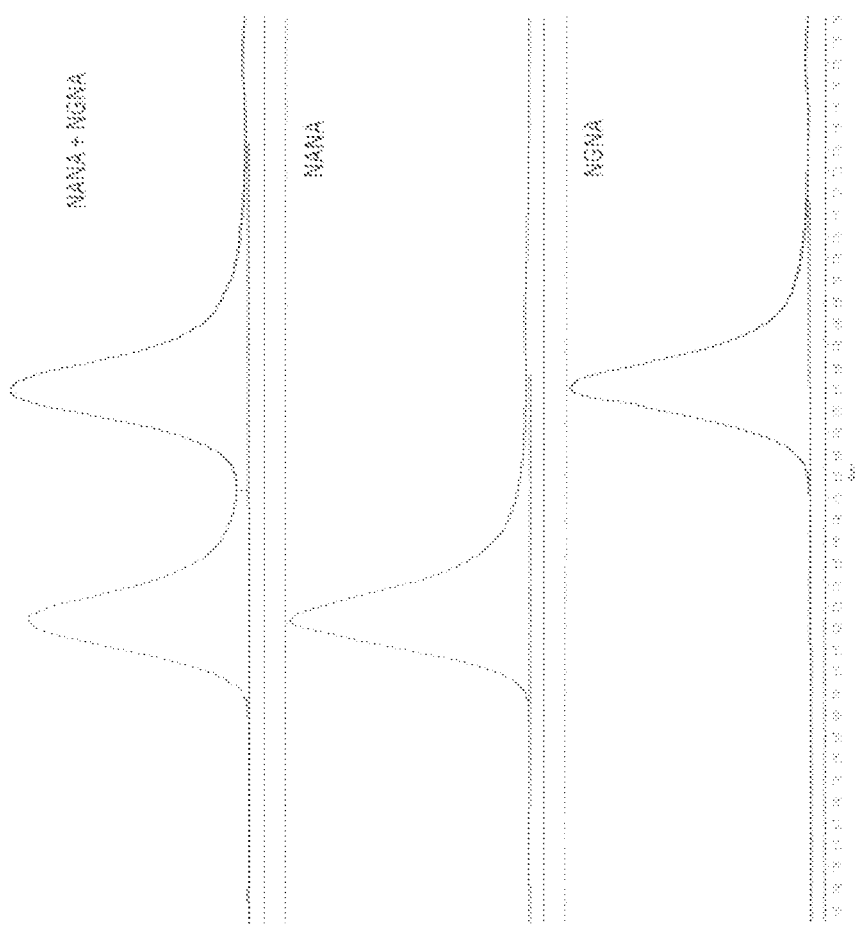

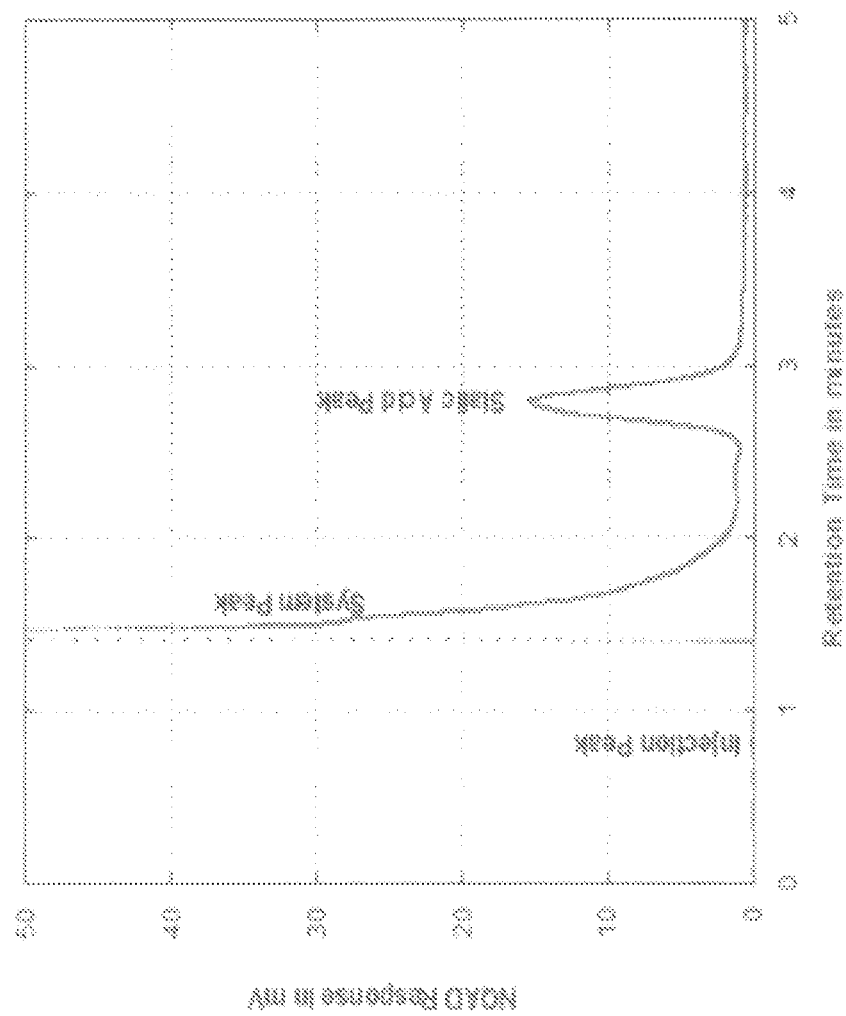
FIG. 3a: Representative Chromatogram of Sialic Acid (NANA) Standard

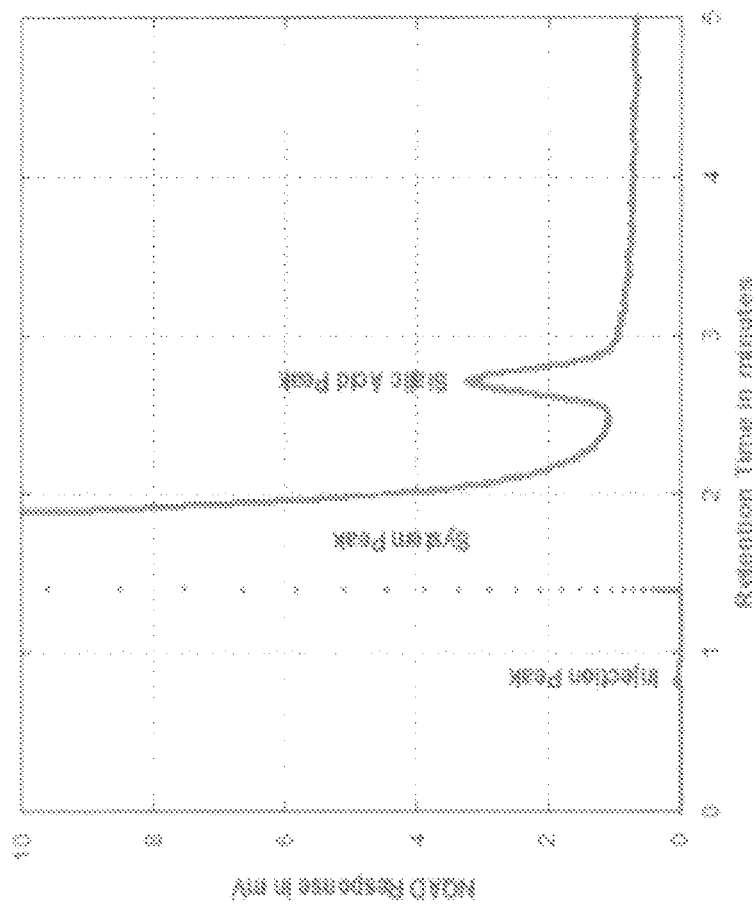
FIG. 3b: Representative Chromatogram of Sialidase A released Sialic Acid (NANA) from glycoprotein-A

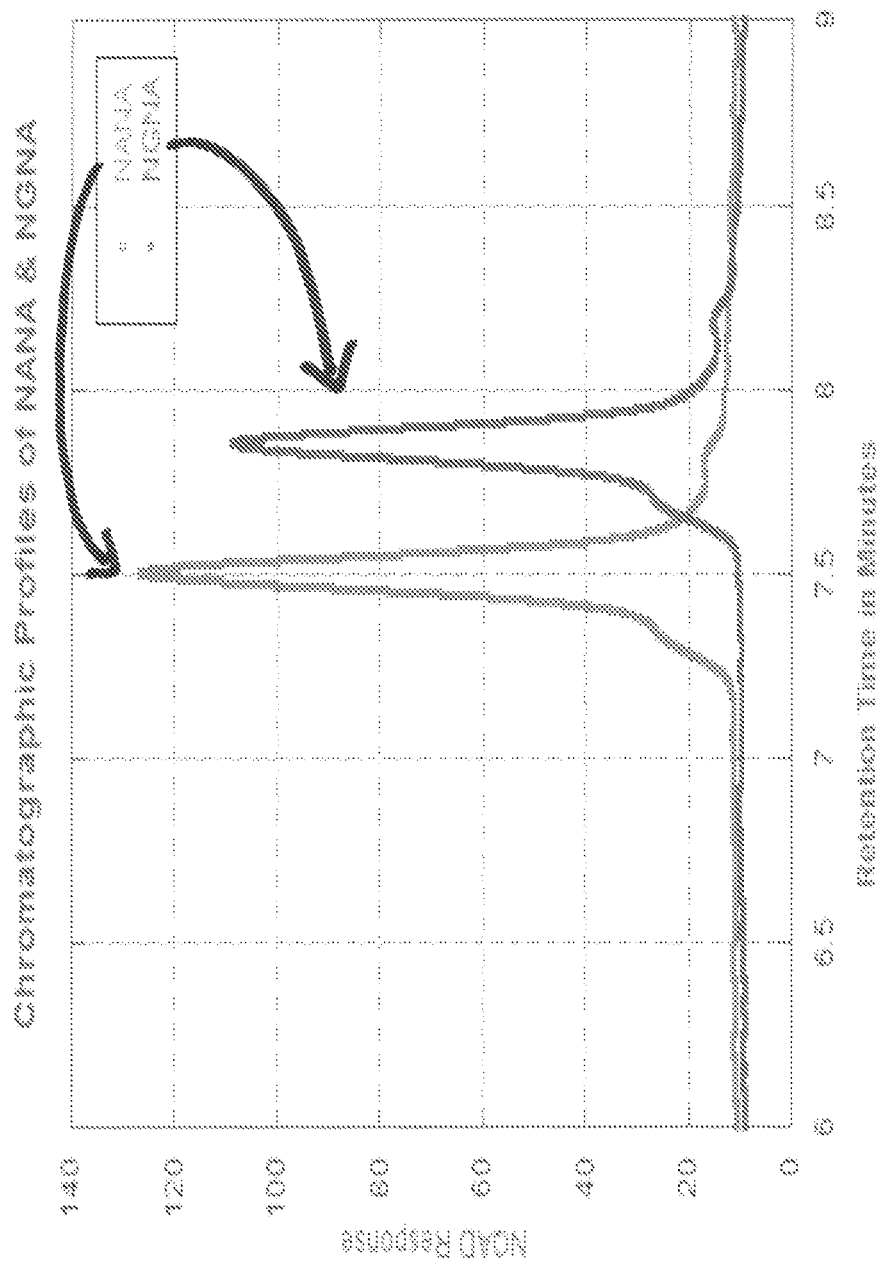
FIG. 4: Chromatogram of NANA-NGNA using 10 cm PolyGLYCOPLEX amide column with 15%B initial gradient composition

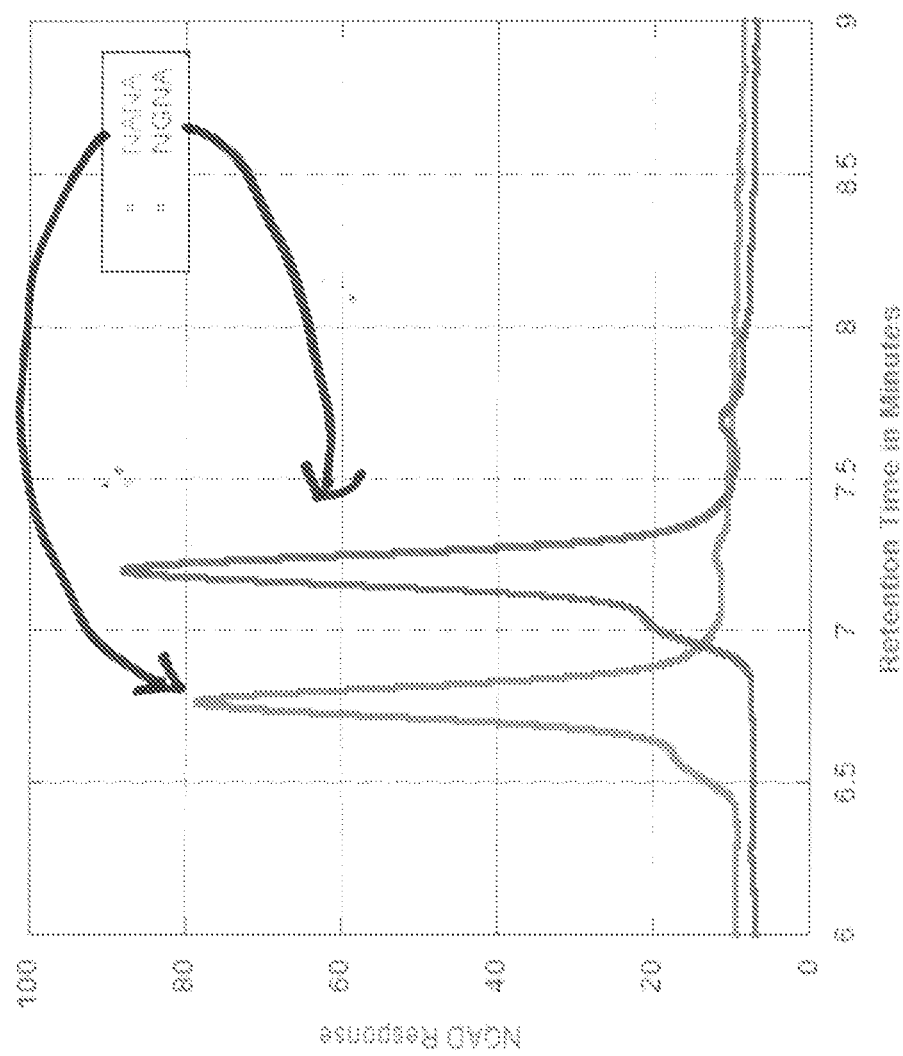
FIG. 5: Chromatogram of NANA/NGNA using 10 cm PolyGLYCOPLEX amide column with 20%B initial gradient composition

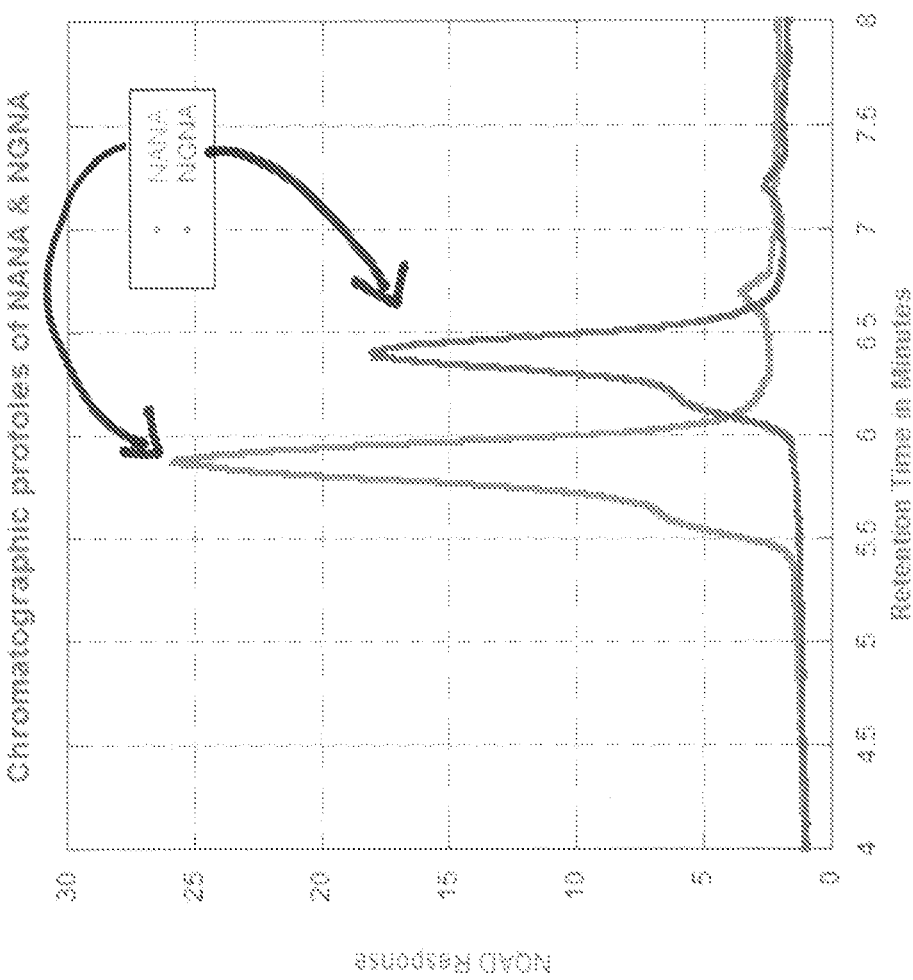
FIG. 6: Chromatogram of NANA/NGNA using 10 cm PolyGLYCOPLEX amide column with 25%B initial gradient composition

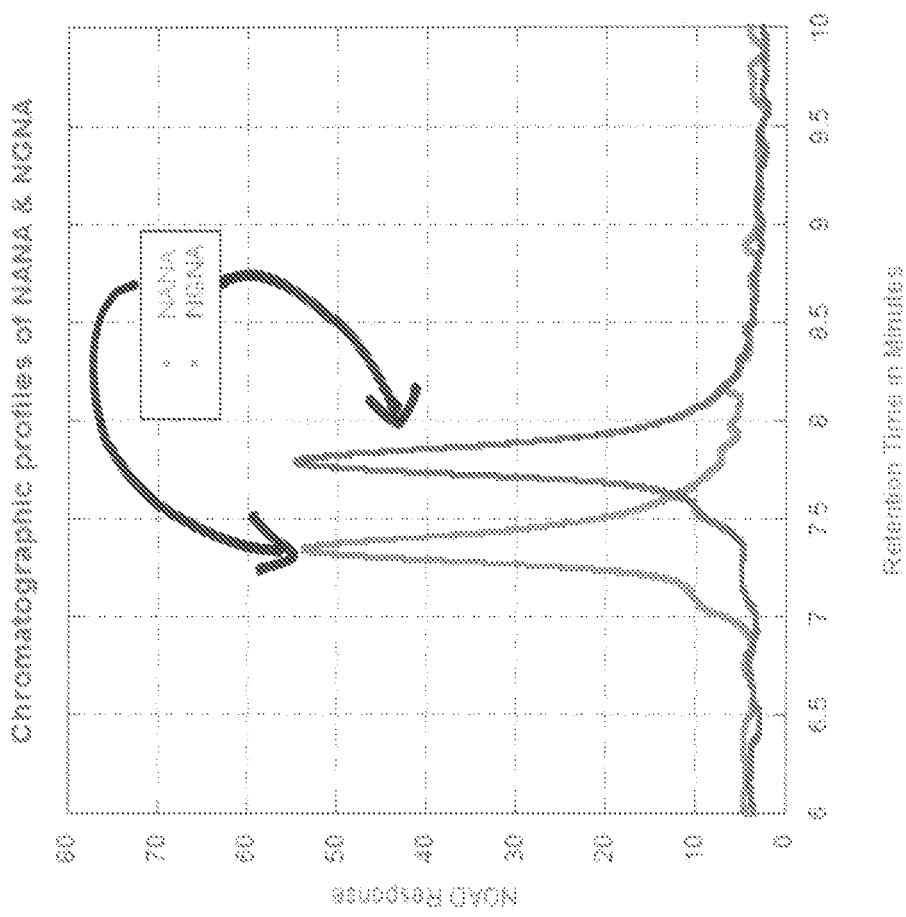
FIG. 7: Separation of NANA & NGNA on 5 cm PolyGLYCOPLEX amide column (100% Acetonitrile and 10% Formic acid as Mobile Phases A & B) w/initial gradient at 20% B

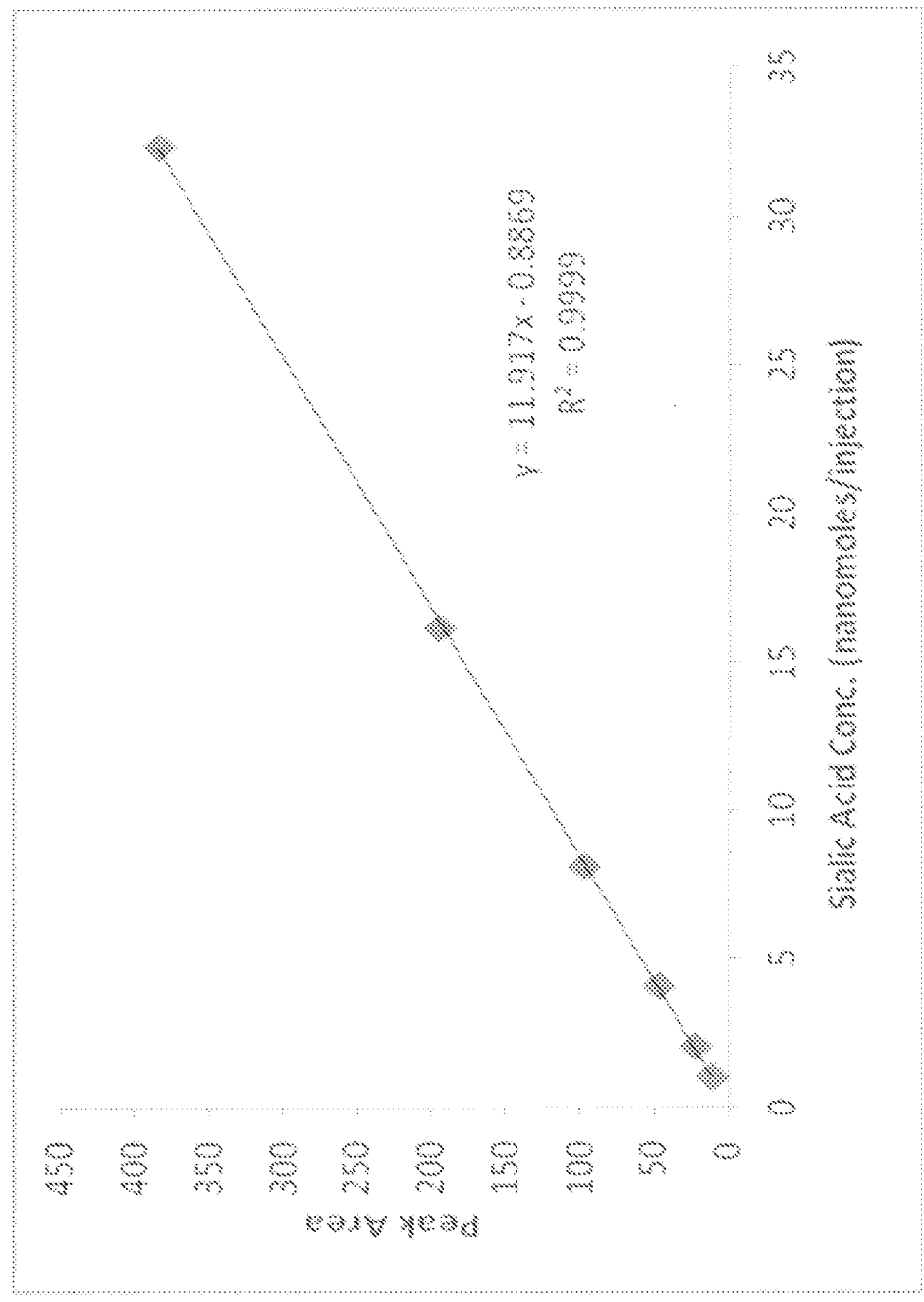
FIG. 8: Linear Regression Plot of Sialic Acid (NANA) Calibration Standards

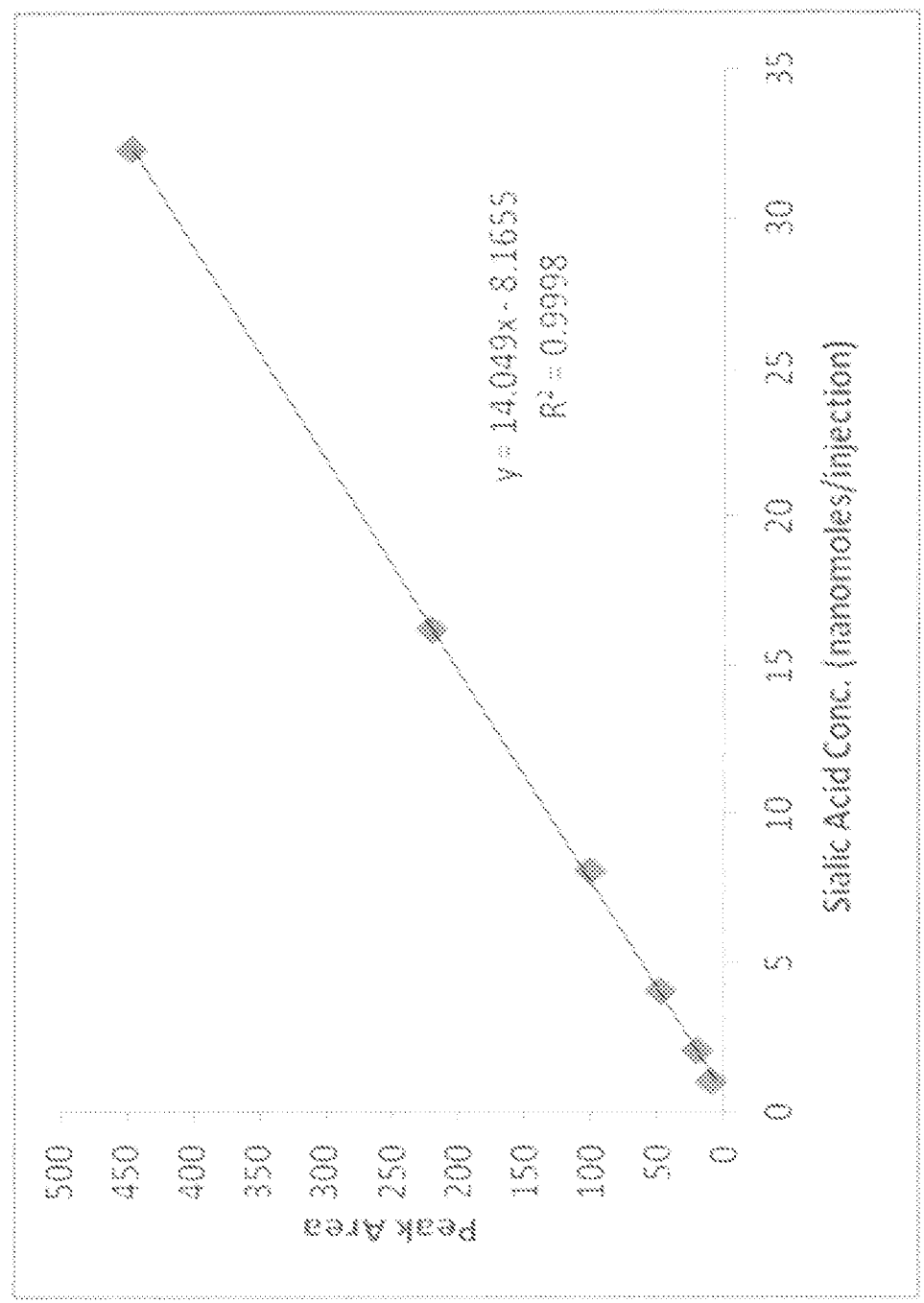
FIG. 9: Linear dynamic range of sialic acid in HPLC/NQAD method

QUANTITATION OF GLYCAN MOIETY IN RECOMBINANT GLYCOPROTEINS

CROSS-REFERENCE TO RELATED APPLICATIONS

This application is a national stage application under 35 U.S.C. § 371 of International Application No. PCT/US2015/061684, having an international filing date of Nov. 19, 2015, which claims the benefit of U.S. Provisional Application No. 62/082,014 filed Nov. 19, 2014, which is incorporated in its entirety by reference herein.

INTRODUCTION

Glycosylation can affect the biological and physiochemical properties of recombinant proteins that are intended for use as biopharmaceutical drugs (Byrne, Donohoe, & O'Kennedy, 2007). For example, the sialic acid moiety of a protein plays a major role in serum half-life. As the terminal galactose becomes exposed, asialolated glycoproteins are endocytosed by hepatic asialo galcotose receptors via receptor-mediated endocytosis (Hildenbrandt & Aronson, 1979).

Accordingly, the status of terminal sialo groups in such biopharmaceutical drugs may require monitoring as an important quality attribute. Commonly employed methods include sialic acid derivatization. In this method, sialic acid is released through acid hydrolysis (e.g., 8M acetic acid) and labeled with a fluorophore or a chromophore such as with 1, 2-diamino-4, 5-methylenedioxybenzene (DMB). Labeling is followed by reversed phase high performance liquid chromatographic (RP-HPLC) analysis.

An alternative approach uses a method in which enzymatically (sialidase-A) released sialic acid is subjected to high pH anion exchange chromatographic (HPAEC) separation and subsequent pulsed amperometric detection (PAD). The HPAEC-PAD system is commercially available from Dionex.

Both methods have drawbacks. The first derivatization technique has inherently high variability, and the second HPAEC-PAD method suffers high variability due to electrode fouling during analysis (Ganesa, Granda, & Mattaliano, 2003). In addition, the materials needed for the HPAEC-PAD method are expensive, and costly to maintain. Therefore, there is a need in the art for a more efficient and reproducible method of assaying for sialic acid moieties on recombinant glycoproteins.

SUMMARY OF THE INVENTION

The invention disclosed herein provides an improved and reliable method for the determination of the glycan moiety on a recombinant glycoprotein. The invention is particularly suitable for determination of sialic acid moiety on a recombinant glycoprotein. The invention is based, in part, on the development of techniques for determining sialic acid moieties on recombinant glycoproteins using water condensation particle counting (WCPC) technology. The WCPC technology allows the analyte to be enlarged using water vapor to provide highest sensitivity. As shown below, the invention allows the determination of type and quantification of sialic acid moieties on recombinant glycoproteins. The recombinant glycoprotein to be analyzed can be, for example, an antibody, a fusion protein, a hormone, a cytokine, or a derivative, variant, mutein, fragment, multimer, or conjugate of any of the preceding molecular entities.

In one aspect, the invention provides a method of determining a glycan moiety on a recombinant glycoprotein, the method comprising digesting the recombinant glycoprotein with an enzyme, preferably an exoglycosidase, to liberate glycan, and quantitating the glycan using condensation nucleation light scattering detection. Optionally, the released glycan acid is separated from the recombinant glycoprotein prior to the quantitating step. The glycan moieties include but are not limited to sialic acid, terminal galactose, N-linked glycans, O-linked glycans and monosaccharide compositional analysis. In one aspect, the condensation nucleation light scattering detection uses a Nano Quantity Analyte Detector (NQAD).

In a preferred aspect, the invention provides a method of determining a sialic acid moiety on a recombinant glycoprotein, the method comprising digesting the recombinant glycoprotein with a sialidase to liberate sialic acid, and quantitating the sialic acid using condensation nucleation light scattering detection. Optionally, the released sialic acid is separated from the recombinant glycoprotein prior to the quantitating step. In one aspect, the condensation nucleation light scattering detection uses a Nano Quantity Analyte Detector (NQAD).

BRIEF DESCRIPTION OF THE FIGURES

FIG. 1: Separation of NANA & NGNA on PolyGLYCOPLEX amide column (Triethyl amine/Acetonitrile under isocratic gradient condition).

FIG. 2A: Chromatogram of NANA/NGNA on 10 cm PolyGLYCOPLEX amide column using 20% Formic Acid.

FIG. 2B: Chromatogram of NANA/NGNA (separate & combined injection) on 10 cm PolyGLYCOPLEX amide column using 20% Formic Acid.

FIG. 3A: Representative Chromatogram of Sialic Acid (NANA) Standard.

FIG. 3B: Representative Chromatogram of Sialidase A released Sialic Acid (NANA) from glycoprotein-A.

FIG. 4: Chromatogram of NANA-NGNA using 10 cm PolyGLYCOPLEX amide column with 15% B initial gradient composition.

FIG. 5: Chromatogram of NANA/NGNA using 10 cm PolyGLYCOPLEX amide column with 20% B initial gradient composition.

FIG. 6: Chromatogram of NANA/NGNA using 10 cm PolyGLYCOPLEX amide column with 25% B initial gradient composition.

FIG. 7: Separation of NANA & NGNA on 5 cm PolyGLYCOPLEX amide column (100% Acetonitrile and 10% Formic acid as Mobile Phases A & B) w/initial gradient at 20% B.

FIG. 8: Linear Regression Plot of Sialic Acid (NANA) Calibration Standards.

FIG. 9: Linear dynamic range of sialic acid in HPLC/NQAD method.

DETAILED DESCRIPTION

As shown herein in one aspect of the invention, derivatization-free analysis of glycoproteins using a HPLC/NQAD method with a PolyGLYCOPLEX™ amide column was well correlated with a HPLC method with pre-column derivatization using 1, 2-diamino-4, 5-methylenedioxybenzene (DMB), as well as the Dionex based high-pH anion-exchange chromatography (or ion chromatography) with pulsed amperometric detection (HPAEC-PAD). However, with the elimination of derivatization step, the HPLC/

NQAD method is more efficient than HPLC/DMB method. In addition, the HPLC/NQAD method is more reproducible than HPAEC-PAD method as the HPAEC-PAD method suffers high variability due to electrode fouling during analysis. Overall, the HPLC/NQAD method disclosed herein as one aspect of the invention offers broad linear dynamic range as well as excellent precision, accuracy, repeatability, reliability and ease of use, with acceptable comparability to the commonly used HPAE-PAD and HPLC/DMB) methods.

Therefore, the methods of the invention include digesting the recombinant glycoprotein with a sialidase to generate sialic acid, and then quantitating the amount and/or type of sialic acid moiety using condensation nucleation light scattering detection.

However, the methods of the invention can also be used to analyze other glycan moieties besides sialic acid, including but not limited to N-glycans, terminal galactose, O-glycans & monosaccharide compositional analysis. Examples of other specific glycan moieties that can be detected, quantified, or analyzed using the methods of the invention include, but are not limited to, glucose (Glu), galactose (Gal), N-acetyl-glucosamine (GlcNAc), mannose, N-acetyl-galactosamine (GalNAc), fucose (Fuc), N-acetyl-mannosamine (ManNAc), fructose, and sucrose, as well as more complex combinations of one or more type of such moieties, such as mono-antennary, bi-antennary, tri-antennary, tetra-antennary, and higher order structures. Any number of post-translational modifications of glycoproteins can similarly be determined and quantitated using the methods of the invention described herein with particularity for sialic acid moieties.

Condensation Nucleation Light Scattering Detection

Condensation nucleation light scattering detection is a type of aerosol based detection technique. A sample to be tested is first nebulized into droplets, and then the mobile phase evaporated from the droplets, leaving suspended particles in air of chemicals with a lower volatility than the mobile phase. This dry aerosol is then moved into another chamber where water vapor is condensed onto the particles, which swell. Swollen particles can be detected individually using a laser based optical sensor. (Gille and Crowshaw, 2008, Chromatography Today v.1(3), p. 26). One commercially available system for condensation nucleation light scattering detection is the Nano Quantity Analyte Detector (NQAD™) from Dionex.

Unlike other aerosol based detectors, condensation nucleation light scattering detection, such as NQAD, doesn't suffer interference from sensor noise or drift that can interfere with the resolution and sensitivity of the analytes. While Refractive Index detectors and other aerosol based detectors are faced with baseline instability and lack of linear response during gradient runs, the NQAD system has been demonstrated to have stable baseline, broader linear dynamic range and has shown to be suitable for the quantitation of analytes in low nanogram levels (Hutchinson, Li, Farrell, Groeber, Szucs, Dicinoski & Haddad, 2011). Evaporative Light Scattering Detector (ELSD) and NQAD are both inexpensive, easy to operate and compatible with all types of HPLC systems. However, for quantitation, NQAD is better suited than ELSD, as it has broader linear dynamic range and higher sensitivity.

According to Hutchinson et al. (2011), limits of detection of UV chromophoric analytes with a variety of physicochemical properties were evaluated using various detectors with different mobile phase compositions under gradient conditions in which NQAD has been demonstrated to be the most sensitive detector. Hutchinson et al. (2011) noted that the lower limit of detection (LLOD) of NQAD was 10 ng/mL, followed by the Corona CAD (Charged Aerosol Detector) with LLOD of 76 ng/mL and the UV detector (at 200 nm) with LLOD of 178 ng/mL at injection volume of 25 µl of analytes consist of various physicochemical characteristics. Based on the study conducted by Olsovská, Kameník and Cajthaml (2009), the investigated antibiotic compounds (w/ low UV absorption)—macrolides (oleandomycin, erythromycin, troleandomycin, clarithromycin and roxithromycin) had exhibited three-fold higher sensitivity with NQAD detection in comparison to the UV detection. With the increased sensitivity of NQAD at the LOD (Limit of Detection) and LOQ (Limit of Quantitation) levels along with the ability of the NQAD to detect non-chromophoric antibiotic compounds had enabled the identification of novel antibiotic compounds (Olsovská, Kameník & Cajthaml, 2009).

Unlike Refractive Index Detectors, conventional Evaporative Light Scattering Detector (ELSD) offers gradient capabilities and adequate sensitivity. However, one drawback of ELSD is that the detector response is exponential, rather than linear (Kimball, Arjo & Johnston, 2004). Data transformation must be applied to the ELSD data response to to generate a linear function. With data tranformation, Evaporative Light Scattering Detectors such as Alltech 800 ELSD and ELSD 3300 have demonstrated excellent linearity in addition to the acceptable accuracy, precision (repeatability and intra-assay precisions), specificity, robustness and stability (Cintron & Risley, 2013). However, NQAD detector has been demonstrated to be 50 and 10 fold more sensitive than ELSD 800 and ELSD 3300 with Limit of Detections (LODs) of 50 g/mL, 10 g/mL and 1 g/mL for ELSD 800, ELSD 3300 and NQAD, respectively.

As shown below, the methods of the invention can be used to identify and quantitate the sialic acid moieties on a recombinant glycoprotein. For example, the amount and/or ratio of liberated N-acetylneuraminic acid and N-glycolylneuramic acid were easily resolved and quantitated using the methods of the invention. Other glycan moieties (e.g., N-linked glycans, terminal galactose, O-linked glycans & monosaccharide compositional analysis) can similarly be determined and quantitated.

Liberating the Glycan Acid Moiety from the Recombinant Glycoprotein

Any appropriate method can be used to target and release the glycan moiety from the glycoprotein. Typically, such methods will include selecting appropriate enzymes that cleave the glycan moiety which one wishes to determine and quantitate. Such enzymes, known as glycosidases, are widely known and commercially available. Examples include but are not limited to: Sialidases; PNGase F, which cleaves all asparagine-linked complex, hybrid, or high mannose oligosaccharides (except those that contain a core of $\alpha(1\text{-}3)$-fucose); Endoglycosidases F1, F2, and F3; Endoglysidase H; O-glycosidase for releasing O-linked glycans; and galactosidase for releasing terminal galactose.

In one of the methods of the invention, the recombinant glycoprotein is digested with a sialidase to liberate sialic acid. The liberated sialic acid can then be detected using condensation nucleation light scattering detection. Any number of commercially available sialydases can be used. The invention is illustrated below using Sialidase-A™ (Prozyme), which releases $\alpha(2\text{-}3)$-, $\alpha(2\text{-}6)$-, $\alpha(2\text{-}8)$, and $\alpha(2\text{-}9)$-linked N-acetylneuraminic acid from complex carbohydrates. However, other sialidases can also be used depending upon the application and the particular sialic acid moiety to be detected on the recombinant glycoprotein.

Separating the Liberated Glycan from the Recombinant Glycoprotein

Optionally, after the glycan moiety is liberated from the recombinant glycoprotein, a separation step can be used in improving the detection capability of the method of the invention. The liberated glycan moiety can be separated by any number of techniques, including but not limited to capillary electrophoresis, filtration, and/or chromatography on the basis of size, charge, hydrophobicity, or a combination thereof. Chromatography can be in a batch or in a column.

In one aspect widely used in quantitation laboratories, the separation step is done using high performance liquid chromatography (HPLC). HPLC columns are available in a wide variety of formats, sizes, and chromatography media. In an embodiment of the invention employing HPLC that is illustrated below, a hydrophilic interaction chromatography (HILIC) step can be used to separate the liberated sialic acid moiety from the recombinant glycoprotein. However, it should be understood that other separation steps can be developed depending upon the glycan moiety or moieties to be analyzed, and the glycoprotein. Loading and elution conditions can make use of various buffers and gradients, depending upon the application selected, and are known to those skilled in the art.

Recombinant Glycoprotein for Use in the Methods of the Invention

For purposes of the invention, a recombinant glycoprotein is defined as any protein that is produced by a host cell that has been engineered to produce the protein by molecular biology techniques such as recombinant DNA (rDNA) technology, whereby the protein has been post-translationally glycosylated. The status of the glycan moiety on a recombinant glycoprotein can be a critical quality attribute, especially for recombinant glycoproteins intended for therapeutic applications (e.g., administration to a mammal). Accordingly, the methods of the invention find particular utility in the manufacture of therapeutic proteins that are recombinant glycoproteins. Just a few examples of such proteins, described in more detail below, are antibodies, fusion proteins, hormones, and cytokines, as well as derivatives, variants, muteins, fragments, multimers, and conjugates thereof.

Nonlimiting examples of recombinant glycoproteins that can be analyzed by the methods of this invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277 (5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of recombinant glycoproteins that can be analyzed according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook, Vols. 1 and 2* (Thompson and Lotze eds., Academic Press, San Diego, Calif., 2003).

Additionally the methods of the invention are useful to analyze glycans released from recombinant glycoproteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other recombinant glycoproteins that can be analyzed using the invention include proteins comprising all or part of the amino acid sequences of differentiation antigens (referred to as CD proteins) or their ligands or proteins substantially similar to either of these. Such antigens are disclosed in *Leukocyte Typing VI (Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.).

The methods of the invention are particularly adapted to analyzing sialic acid moieties on recombinant glycoproteins that are fusion proteins. The fusion proteins can comprise all or a portion of any of the above proteins fused to another protein or protein domain. Particularly useful fusion proteins are Fc fusion proteins. A number of such fusion proteins are available on the market, or are in development. Examples of fusion proteins that can be analyzed using the methods of the invention include but are not limited to etanercept, aflibercept, rilonacept, belatacept, abatacept, and alefacept.

Enzymatically active recombinant glycoproteins or their ligands can also be analyzed using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

Recombinant proteins that are antibodies can also be analyzed using the methods of the invention. The term "antibody" refers to immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD19, CD20, CD22, CD23, CD25, CD27L, CD32, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-12, IL-12 p35 subunit, IL-13, IL-21, IL-23, IL-23 p19 subunit, IL-12/IL-23 shared p40 subunit, IL-2 receptor, IL-4 receptor, IL-6 receptor, IL-13 receptor, IL-17 receptor, IL-18 receptor subunits, FGL2, PDGF-β and analogs thereof (see U.S. Pat. Nos. 5,272,064 and 5,149,792), B7RP-1, B7RP-2, VEGF, TGF, TGF-β2, TGF-β1, c-fms, EGF receptor (see U.S. Pat. No. 6,235,883), CGRP receptor, VEGF receptor, hepatocyte growth factor, proprotein convertase subtilisin/kexin type 9 (PCSK9), FGF21, osteoprotegerin ligand, interferon gamma, EGFRvIII, B lymphocyte stimulator (BlyS, also known as BAFF, THANK, TALL-1, and zTNF4; see Do and Chen-Kiang (2002), Cytokine Growth Factor Rev. 13(1): 19-25), BAFF Receptor, BCMA, April, ST2, C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TSLP, IFNγ, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), angiopoietin 1 (Ang1), angiopoietin 2 (Ang2), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), programmed cell death 1 (PD-1), programmed cell death ligand 1 (PDL-1), programmed cell death ligand 2 (PDL-2), lymphocyte activation gene-3 (LAG-3), T-cell immunoglobulin domain and mucin domain 3 (TIM3), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be analyzed using the methods of the invention include but are not limited to adalimumab, alirocumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, dupilumab, eculizumab, gemtuzumab guselkumab, ozogamicin, golimumab, ibritumomab, ixekizumab, ipilimumab, tiuxetan, labetuzumab, lebrikizumab, mapatumumab, mavrilimumab, matuzumab, mepolizumab, motavizumab, muromonab-CD3, nivolumab, natalizumab, nimotuzumab, ofatumumab, omalizumab, oregovomab, palivizumab, panitumumab, pemtumomab, pertuzumab, pembrolizumab, ranibizumab, rituximab, romosozumab, rovelizumab, rilotumumab, tildrakizumab, tocilizumab, tositumomab, tralokinumab, trastuzumab, tremelimumab, ustekinumab, vedolizomab, zalutumumab, and zanolimumab.

Examples of cytokines that are glycoproteins according to the invention include, but are not limited to, IL-1α, IL-1β, IL-2, IL-3, IL-7, IL-4, IL-5, IL-6, IL-8, IL-10, IL-12, IL-12 p35 subunit, IL-13, IL-17 (including, but not limited to, monomers, homodimers, and heterodimers of IL-17A, IL-17B, IL-17C, IL-17D, and IL-17E (also known as IL-25)), IL-21, IL-23, IL-23 p19 subunit, and IL-12/IL-23 shared p40 subunit.

The invention having been described, the following examples are offered by way of illustration, and not limitation.

EXAMPLES

Abbreviations

ACN: Acetonitrile
AEX: Anion Exchange Chromatography
CAD: Charged Aerosol Detector
CEX: Cation Exchange Chromatography
CNLSD: Condensation Nucleation Light Scattering Detection
DMB: 1, 2-diamino-4, 5-methylenedioxybenzene
ELSD: Evaporative Light Scattering Detector
HIC: Hydrophobic Interaction Chromatography
HILIC: Hydrophilic Interaction Chromatography
HPAEC-PAD: Anion-exchange chromatography and pulsed amperometric detection
LLOD: Lower limit of detection
LOD: Limit of Detection
LOQ: Limit of Quantitation
NANA: N-acetylneuraminic acid
Neu5Ac N-acetylneuraminic acid
NGNA: N-glycolylneuraninic acid
NQAD: Nano Quantity Analyte Detector
PAD: Pulsed Amperometric Detector
RP-HPLC: Reversed Phase High Performance Liquid Chromatography
TFA: Trifluoroacetic Acid
WCPC: Water based Condensation Particle Counting
LCMS: Liquid chromatography-mass spectrometry
Methods & Materials PolyGLYCOPLEX amide columns (50×4.0 mm w/5μ) and (100×2.1 mm, 5μ) were purchased from PolyLC. XBridge C18 Column (4.6×250 mm w/5μ) and YMC-Pack ODS-AQ Analytical Column (2.0×150 mm w/3μ) were purchased from Waters. Kinetex C18 column (4.6×100 mm w/2.6μ) and a mixed mode (Size Exclusion/Ion-chromatography) sugar column (8.0×300 mm w/6μ) were purchased from Phenomenex and Shodex, respectively. Anion and cation exchange columns (4.6×150 mm w/3μ) were purchased from Sepax Technologies. Sodium 1-heptanesulfonate, trimethyl tetradecyl ammonium hydrogen sulfate, L-glutamic acid, L-aspartic acid, NANA and NGNA were purchased from Sigma Aldrich. Sialidase-A was purchased from Prozyme. HPLC auto-sampler vials, glass inserts and vial caps were purchased from Agilent. Two in-house glycoproteins (Glycoproteins A & B) containing N and O-linked sialic acid (NANA) were used as model proteins for the study.

Example 1

1. Initial Screening of HPLC Columns with Various Chemistries

Selection of an appropriate column is an important part of any HPLC method development. Therefore, an exhaustive evaluation of multiple column chemistries was carried out. In order to retain and quantitate sialic acid, various RP-HPLC columns including X-bridge C18 column, YMC-Pack ODS-AQ C18 column and Kinetex C18 column were evaluated under acidic (0.1% TFA and 0.1% TFA/ACN as mobile phases A & B, respectively) and neutral (50 mM phosphate buffer, pH 7.0 and ACN as the initial and elution mobile phases, respectively) mobile phase conditions. An evaluation was also carried out at an intermediate pH using 10 mM triethylamine phosphate at pH 4.4 as initial mobile phase and acetonitrile as elution mobile phase. In all cases, isocratic gradient at 5% B was maintained initially for 5 minutes prior to applying a linear gradient at a 4% increment per minute until 95% B was reached. A flow rate of 1 mL/min was applied in all cases.

Since RP-HPLC analysis in the presence of appropriate ion-pair reagents can increase the retention of charged analytes (Sharma, Glick, & Vouros, 2012) like sialic acid, ion-pair chromatography also was explored by adding either a positively charged cationic ion-pair reagent or negatively charged anionic ion-pair agent to the mobile phase at a final concentration of 5 mM. Sodium 1-heptanesulfonate solution was used as cationic ion-pair reagent (Calhoun & King, 2007) and trimethyl tetradecyl ammonium hydrogen sulfate as anion pair reagent (Remsburg, 2007). Ion-pair chromatographic analyses were carried out on X-bridge C18 column using 0.1% TFA w/5 mM ion-pair reagent as mobile phase A and 0.1% TFA w/5 mM ion pair-reagent/ACN as elution mobile phase B. In all cases a linear gradient from 5% B to 95% B was applied over the course of 20 minutes. As described by Isakau, Robert and Shingel (2009), a mixed mode Size Exclusion/Ion-chromatography (SEC/IEX) sugar column from Shodex was evaluated under isocratic mode at 1 mL/min flow rate using 50% methanol as mobile phase. Such SEC/IEX chromatography has been recognized as an effective technique for simultaneous determination of anions and cations after a single sample injection into the separation column (Mori, Taoda, Itabashi, Ikedo, & Tanaka, 2006). Sialic acid (NANA) standard at a concentration of 1 mg/mL was serially diluted down to 0.0156 mg/mL and from which 100 μl of each standard was injected.

As the NQAD detector is not compatible with high salt, AEX and CEX columns were evaluated using pH gradient instead of salt gradient. Ion exchange chromatography was performed under pH gradient using cation and anion columns from Sepax. With the known pKa (2.6) of sialic acid (NANA), a linear pH gradient starting from pH 2.2 ending in pH 3.6 using 10 mM Glycine/HCl was applied for the anion exchange chromatography and a linear gradient from pH 3.6 to pH 2.2 using 10 mM Glycine/HCl was applied for the cation exchange chromatography. All analyses were carried out on Agilent 1100 or 1200 systems equipped with NQAD from QUANT technologies.

RESULTS: Evaluation results of various separation techniques suggested that quantitation of non-derivatized sialic acid was not feasible with chromatographic techniques such as RP-HPLC, Ion-pair chromatography, mixed mode Size Exclusion/Ion-chromatography and Ion-Exchange chromatography (under the pH gradient mode). Results obtained from the evaluation of RP-HPLC columns have suggested that highly polar sialic acid could not be retained under acidic, neutral or intermediate pH conditions. The observed phenomenon was not unexpected as the highly enriched polar groups on sialic acid (carbonyl, oxyl, carboxylic, amine and multiple hydroxyls) inhibit its binding to RP-HPLC columns. Although RP-HPLC columns facilitate the retention of highly hydrophobic fluorescent labeled sialic acid (Zauner, Deelder & Wuhrer, 2011), highly polar non-derivatized sialic acid is difficult to retain on a RP-HPLC column. The attempt that was made to increase the hydrophobicity of sialic acid with the aid of ion-pair reagents was unsuccessful. RP-HPLC analysis of sialic acid in the presence of cation and anion ion-pair reagents did not help to improve the retention of non-derivatized sialic acid to RP-HPLC column. Although the attempted approaches should have been worked on theoretical grounds, the negative outcome could have resulted from the fact that the vendor recommended amount of 5 mM ion pair reagent may not have been sufficient for adequate binding. Based on published literature, the amount of ion-pair reagents should be significantly higher for highly polar molecules like sialic acid. For example, 60 mM aqueous solution of triisopropanolamine ion-pair reagent was used for the determination of sialic acids in biological fluids using reversed-phase ion-pair chromatography (Siskos & Spyridk, 1999). Increasing the amount of ion-pair reagents can be explored.

Evaluation results of mixed mode Size Exclusion/Ion-chromatography sugar column (dimension 8×300 mm) indicated that the method sensitivity was not sufficient for the intended application. Sialic acid standard with concentrations ≤1 mg/mL did not exhibit any peak at 100 μl injection onto this column. As the detection threshold of the method is below the desired range (0.015 to 1.0 mg/mL), further optimization of this method was not pursued. The same column with a smaller dimension could help to improve the sensitivity of the method. However, columns with smaller dimensions are not yet available. Chromatograms obtained from any of the above mentioned analyses are not shown as none of them exhibited any peaks other than the injection peaks.

Stationary phases containing polymeric structures of poly-succinimide derivatives with functional groups such as PolyGLYCOPLEX, PolySulfoethyl aspartamide, and Poly-Hydroxyethyl aspartamide are better suited as they are widely used to separate various highly polar compounds (Ikegami, Tomomatsu, Takubo, Horie, & Tanaka, 2008).

Example 2

2. Evaluation of PolyGLYCOPLEX Amide Column for separating NANA-NGNA

This evaluation was to assess the use of a PolyGLYCOPLEX amide column for the separation and quantitation of NANA and NGNA in proteins containing both forms of sialic acids. Although RP-HPLC methods are suited for retaining highly hydrophobic fluorescent labeled sialic acid (Zauner, Deelder & Wuhrer, 2011), highly polar non-derivatized sialic acid is difficult to retain on RP-HPLC column. Therefore, HILIC chromatography was explored. Stationary phases containing polymeric structures of poly-succinimide derivatives with functional groups such as PolyGLYCOPLEX, PolySulfoethyl aspartamide, and PolyHydroxyethyl aspartamide have been used to separate various highly polar compounds (Ikegami, Tomomatsu, Takubo, Horie, & Tanaka, 2008). PolyGLYCOPLEX amide column (100×2.1 mm, 3μ) from PolyLC was evaluated under isocratic condition using the mobile phase containing acetonitrile w/10 mM triethylamine phosphate (80:20 v/v) at pH 4.4. NANA and NGNA standards at 1 mg/mL were diluted 1:10 with water first and then the two standards were mixed at 1:1 ratio before 10 μL injections were made. Subsequent to the injection of NANA-NGNA mixture, 5 μL each of NANA NGNA standards also were injected separately. Analyses were carried out on the Agilent 1100 system using the NQAD setting shown below.

| NQAD Parameters | |
|---|---|
| Gauge setting for gas pressure | 30 PSI |
| Evap Temperature | 35° C. |
| Nebulizer Temperature | 25 |
| Set Filter | 1X |
| Off Se | 0% |
| Effluent Flow | 1.5 mL/min |
| Linearization | On |
| Optic temperature | 60° C. |
| Growth Temperature | 60° C. |
| Conditioner Temperature | 20° C. |

RESULTS: As depicted in FIG. 1, analysis carried out on PolyGLYCOPLEX amide column using acetonitrile w/10 mM Triethylamine phosphate at pH 4.4 under isocratic condition provided excellent separation between NANA and NGNA. Peak assignments were done by injecting NANA and NGNA separately. However, the extent of carryover was so severe (data not shown) that if NGNA is injected subsequent to NANA, we could not get a clean NGNA chromatogram w/o having trace level of NANA and vice versa. The carryover issue along with the run to run variability inherent to the isocratic methods prompted us to disregard this method. Although a column cleaning protocol can be developed and adopted to resolve the carry over issue, it can affect the accuracy of quantitation results.

Example 3

3. Optimization of PolyGLYCOPLEX Method for NANA-NGNA Separation

Evaluation results of 5 & 10 cm PolyGLYCOPLEX amide columns under different mobile phase conditions are shown in sections 3.1 through 3.4. Evaluation results of Evaporator Temperatures are shown in section 3.5.

3.1 Optimization of Chromatography

In this example, we evaluated and optimized the PolyGLYCOPLEX Amide column under different mobile phase conditions and various NQAD evaporator temperature settings. Since PolyGLYCOPLEX Amide column outperformed other column chemistries in terms of retaining non-derivatized sialic acid, PolyGLYCOPLEX Amide column was selected for further optimization to achieve best possible separation between NANA and NGNA without having the issue of carryover. While this section (section 3.1) details chromatographic optimization of the method, section 3.2 describes the conditions used for optimizing NQAD Evaporator Temperature. Different chromatographic conditions evaluated are as listed below.

- 10 cm PolyGLYCOPLEX column w/100% ACN and 10% formic acid as mobile phases
- 10 cm PolyGLYCOPLEX column w/100% ACN and 0.1% TFA as mobile phases
- 5 cm PolyGLYCOPLEX column w/100% ACN and 10% formic acid as mobile phases
- 10 cm PolyGLYCOPLEX w/ACN and 20% formic acid as mobile phases A 10 cm or 5 cm PolyGLYCOPLEX Amide column was evaluated using ACN as initial mobile phase. Elution mobile phases of either formic acid or 0.1% TFA as listed above were used. NANA standard at 1 mg/mL was diluted 1:10 with water and injections were made at 0, 2, 4, 6, 8 and 10 μL. In addition to that, NANA and NGNA standards were injected (same sample prep as in section 2) to evaluate the method's capability to separate NANA and NGNA. Analyses were carried out on the Agilent 1200 system. NQAD parameters are same as in section 2. Multiple experiments were carried out by changing the composition of the initial gradient, ranging from 0% B to 35% B. In all cases, the initial % B was held constant for 1 minute prior to applying 15 minute linear gradient until 95% B was attained. Column temperature was kept at ambient and the flow rate was maintained at 0.5 mL/min.

RESULTS: Out of various initial gradient compositions that were evaluated, a 20% initial gradient composition appears to be slightly better in terms of separation between NANA and NGNA. A representative chromatogram of NANA-NGNA separation using 10 cm PolyGLYCOPLEX amide column (using 100% Acetonitrile and 10% Formic acid as Mobile Phases A & B) at initial gradient compositions of 15, 20 and 25% are shown in FIGS. 4, 5, and 6, respectively.

Unlike the carry over issue encountered previously in the isocratic run (section 1), no such carry over was observed under any of the gradient conditions evaluated. Evaluation of 10 cm PolyGLYCOPLEX amide column using 100% acetonitrile and 0.1% trifluro acetic acid as Mobile Phases A & B gave baseline noise and peak symmetry that was less than desirable. Evaluation results of 5 cm PolyGLYCOPLEX amide column using 100% Acetonitrile and 10% formic acid as Mobile Phases A&B gave separation between NANA and NGNA (FIG. 7) that was not as good as the separation achieved on the 10 cm PolyGLYCOPLEX amide column under the same analysis conditions (FIG. 5). Evaluation of 10 cm PolyGLYCOPLEX amide column using 100% acetonitrile and 20% formic acid as mobile phases A & B indicated that 20% formic acid as mobile phase B is better than 10% formic acid in terms of achieving sharper peaks and slightly better separation between NANA and NGNA (FIG. 2A vs. FIG. 5). FIG. 2B depicts chromatogram of NANA and NGNA injected separately as well as a mixture. Chromatogram overlay of NANA standard at multiple concentrations was tested, and no carryover issue was encountered.

3.2 Optimization of NQAD Evaporator Temperature

Evaporator temperature (the most critical parameter of NQAD) was optimized to maximize the evaporation of the solvent from the eluent while maintaining minimal volatility of sialic acid to achieve optimum signal to noise ratio. Other temperature settings (Nebulizer temperature, Optic temperature, growth temperature and conditioner temperature) are constant and cannot be varied. Evaporator temperature setting was varied from 35 to 60° C. (35, 40, 45, 50, 55 & 60° C.) to determine the optimum Evaporator temperature at which best signal to noise can be achieved. Evaluation was carried out using PolyGLYCOPLEX Amide column (50×4 mm, 5 g) with 100% ACN and 20% formic acid as mobile phases A & B, respectively. All NQAD parameters except for the Evaporator temperature were the same as in Example 2. Initial mobile phase composition of 20% B was maintained for 1 minute before the gradient was applied. A linear increment of 8.3% B/min was applied such that 95% B was reached at 10 minutes. Column temperature was kept at ambient and column flow rate was maintained at 1.0 ml/min.

RESULTS: The signal intensity as well as the baseline noise was directly proportional to the degree of Evaporator temperature. Optimum signal to noise ratio was achieved at evaporator temperature of 40° C.

Example 4

4. Short PolyGLYCOPLEX Amide Column for Quantitation of NANA

To quantitate NANA in samples in which NGNA is absent, a short (50×4.6 mm, 3 µm) PolyGLYCOPLEX amide column was evaluated. In order to increase the column life, lower percentage of formic acid was used as the elution mobile phase instead of 20% formic acid. As lower percentage of formic acid is not strong enough to elute highly polar sialic acid from PolyGLYCOPLEX amide column, evaluation was carried out under a novel gradient approach. In this approach, the mobile phase gradient was switched from initial mobile phase to elution mobile phase as soon as the injection was made such that that the bound sialic acid elutes in an isocratic environment of the elution mobile phase. Evaluation was carried out to determine optimum mobile phase compositions and flow rate as well as best gradient. PNGaseF released NANA was subjected to HPLC/NQAD analysis before and after filtration to determine the need for filtration. Detailed evaluation parameters are described in sections 4.1 through 4.4.

Evaluation results of short PolyGLYCOPLEX amide column (50×4.6 mm, 3 µm) with lower percentage of formic acid as elution mobile phase is suitable for the quantitation of NANA as long as the switching from initial mobile phase condition to elution mobile condition occurs soon after the injection was made. Under this gradient condition, stable baseline and adequate peak symmetry are achieved as the elution of sialic acid (NANA) is occurring during the isocratic environment of the elution mobile phase. Analysis results of different elution mobile phases, different gradient conditions and different flow rates shown in sections 4.1 through 4.3 indicated that best results are achieved with 1% formic acid at a flow rate of 1.5 mL/min with the use of gradient 2. Results shown in section 4.3 suggested that sample filtration subsequent to PNGaseF is not required. Representative chromatograms of sialic acid (NANA) standard and PNGaseF released sialic acid (NANA) from glycoproteins using the optimized conditions are shown in FIGS. 3A & 3B, respectively. A representative linear regression plot of NANA standards are shown in FIG. 8.

4.1 Evaluation of 0.5% Formic Acid Vs. 1.0% Formic Acid

While 100% acetonitrile was used as initial mobile phase, 0.5% or 1.0% formic acid was used as elution mobile phase for this set of experiments. All NQAD parameters except for the Evaporator temperature were same as in section 2. The optimized Evaporator temperature of 40° C. was applied. The gradient switching from mobile phase A (100% ACN) to mobile phase B (1.0% formic acid) was prompted to occur 1 minute after the injection. Subsequent to the gradient switching, isocratic condition at 1.0% formic acid was maintained for 10 minutes. Column temperature was kept at ambient and flow rate was maintained at 1.0 ml/min.

RESULTS: Overlaid and stacked chromatograms of two elution mobile phase (0.5% and 1% Formic acid as elution mobile phases) demonstrated that the chromatogram generated with 1% formic acid has exhibited better peak symmetry than with 0.5% formic acid, thus, 1% formic acid was selected over 0.5%.

4.2 Evaluation of Gradients 1 & 2

All parameters except for the HPLC gradient were same as in section 4.1. 100% ACN and 1.0% formic acid were used as mobile phases A & B, respectively. While the gradient switching from 100% ACN to 1.0% formic acid was prompted to occur within 1.0 minute for gradient 2, the duration for gradient switching was shortened from 1.0 minute to 0.1 minute for gradient 1.

RESULTS: The chromatograms obtained from gradient 1 (quick gradient switch from initial mobile phase to elution mobile phase in 0.1 minute) and gradient 2 (gradient switch from initial mobile phase to elution mobile phase in 1.0 minute) were not very different from each other. However, the gradient 2 with longer retention time was selected because the separation between sialic acid and system suitability standards (L-glutamic acid and L-aspartic acid elute) is better with gradient 2.

4.3 Evaluation of Different Flow Rates

HPLC gradient 2 described in section 4.2 was applied at multiple flow rates (1.0, 1.2 & 1.5 mL/min) using 100% acetonitrile and 1.0% formic acid as mobile phases A and B, respectively. All NQAD parameters were the same as in section 4.1.

RESULTS: Analyses carried out under different flow rates showed that the best peak symmetry is achieved at 1.5 mL/min flow rate.

4.4 Evaluation of Filtered Vs. Non-Filtered Sample Digest

Samples digested with sialidase were injected with and without centricon filtration. The intent of centricon filtration was to separate out sialic acid (NANA) from interfering protein and other matrix components. Analysis was carried out on a 5 cm PolyGLYCOPLEX amide column using optimized HPLC gradient and NQAD settings shown below. 100% acetonitrile and 1.0% formic acid were used as mobile phases A and B, respectively.

| HPLC Gradient | |
| --- | --- |
| Time | % B |
| 0 | 0 |
| 1.0 | 100 |
| 10 | 100 |

Column Temperature: Ambient
Flow Rate: 1.5 mL/min
Detection: NQAD

| NQAD Settings | |
| --- | --- |
| Gauge setting for gas pressure | 30 PSI |
| Evap Temperature | 40° C. |
| Nebulizer Temperature | 25 |
| Set Filter | 1X |
| Off Set | 0% |
| Effluent Flow | 1.5 mL/min |

NANA standards in the range of 1 to 32 nmol/20 μl injection were prepared from lyophilized NANA standard from Sigma. A system suitability standard was tested as it is an integral part of many analytical procedures to ensure the performance validity of the integrated system that consists of equipment, electronics, analytical operations, and samples to be analyzed. Injection of 20 μl of system suitability mixture, consisting of 1.0 mg/mL each of L-glutamic acid and L-aspartic acid, was included in each analytical run.

RESULTS: Chromatographic profiles as well as the peak responses of NANA was comparable between filtered and non-filtered samples. In order to achieve higher efficiency during analysis, time consuming filtration alternative can be opted out as it is evident that NANA quantitation is not interfered by residual protein and other matrix components.

Example 5

5. Comparability Assessment of HPLC/NQAD Method Vs. Other Orthogonal Methods

The short HPLC method with gradient 2 described in section 4.2 at a flow rate of 1.5 mL/min. was compared against the HPAEC-PAD & HPLC/DMB methods to determine how well the results obtained from HPLC/NQAD method correlate.

5.1 Sample Preparation for HPLC/NQAD, HPAEC-PAD & HPLC/DMB Analyses:

For the comparative study, method specific techniques were used for releasing NANA from glycoprotein. Enzymatic digestion conditions used for HPLC/NQAD and HPAEC-PAD are described in sections 5.1.1 and 5.1.2, respectively. Acid hydrolysis and subsequent DMB derivatization performed for HPLC/DMB method is described in section 5.1.3. Calculation steps for determining picomoles of NANA per injection are shown as follows.

$$\text{Pmole } NANA/inj = \frac{X.XX\ \mu g^*}{\mu L\ NANA}\ \frac{1\ \mu mol^*}{309.27\ \mu g}\ \frac{10^6 pmol^*}{1\ \mu mol}\ 20\ \mu L\ (vol.\ injected)$$

Where $X.XX$ μg is the amount of NANA injected and 309.27 μg is the molecular weight of NANA Equations used for determining picomoles of protein per injection as well as picomoles of NANA/picomoles of protein are as shown in sections 5.1.1 through 5.1.3.

5.1.1 Sialidase-A Digestion of Samples for HPLC/NQAD Method:

For enzymatic digestion, 10 μl of a 5.0 mg/mL sample (50 μg) was mixed with 12 μl sialidase-A (Prozyme) and 4 μl 5× reaction buffer and 4 μl Milli-Q water. Samples were incubated in a 37° C.±3° C. water bath for 4 hours±15 minutes, which was established as the optimum digestion condition through reaction time course. At the end of incubation 30 μl water was added to bring the total volume to 60 μl. Following equation was used for the calculation of picomoles of protein per injection for the HPLC/NQAD method:

5.0 mg/mL*10 μL*(1 μmol/MW in μg)*(10⁶ picomol/μmol)*(1/60 μL)*20 μL

Where, 5.0 mg/mL is the concentration of sample, MW is the protein molecular weight, 60 μL is the final volume of sample, and 20 μL is the injection volume.

Picomoles of NANA/picomoles of protein is determined by dividing picomoles of NANA/inj. calculated based on the equation presented in section 5.1 divided by X1 picomoles/inj. calculated from section 5.1.1.

5.1.2 Sialidase-A Digestion of Samples for HPAEC-PAD Method:

In order to release the sialic acid from glycoprotein samples, 10 μl of a 1.0 mg/mL sample was mixed with 2 μl sialidase-A (Prozyme) and 4 μl 5× reaction buffer and 4 μl Milli-Q water. Samples were incubated in a 37° C.±2° C. water bath for 4 hours±15 minutes, which was established as the optimum digestion condition through reaction time course. At the end of incubation 780 μl water was added to bring the total volume to 800 μl. The following equation was used for the calculation of picomoles of protein per injection for HPAEC-PAD method:

1.0 mg/mL*10 μL*(1 μmol/MW in μg)*(10⁶ picomol/μmol)*(1/800 μL)*20 μL

Where, 1.0 mg/mL is the concentration of sample, MW is the protein molecular weight, 800 μL is the final volume of sample, and 20 μL is the injection volume.

Picomoles of NANA/picomoles of protein is determined by dividing picomoles of NANA/inj. calculated based on the equation presented in section 5.1 divided by X2 picomoles/inj calculated from section 5.1.2.

5.1.3 Acid Hydrolysis and DMB Derivatization for HPLC/DMB Method:

N-acetylneuraminic acid (NANA) from glycoprotein samples were released through 8M acetic acid hydrolysis followed by pre-column derivatization with fluorescent reagent 1, 2-diamino-4, 5-methylenedioxybenzene (DMB). N-Acetylneuraminic acid forms highly fluorophoric quinoxalinone derivative when treated with DMB (Lin, Inoue & Inoue, 2000). Following equation was used for the calculation of picomoles of protein for HPLC/DMB method.

1.0 mg/mL*10 μL*(1 μmol/MW in μg)*(10⁶ μmol/μmol)*(1/60 μL)*20 μL

Where, 1.0 mg/mL is the concentration of sample, MW is the protein molecular weight, 60 μL is the final volume of sample, and 20 μL is the injection volume.

Picomoles of NANA/picomoles of protein is determined by dividing pmole of NANA/inj. calculated based on the equation presented in section 5.1 divided by X3 pmol/inj calculated from section 5.1.3.

5.2 Sample Analysis & Comparability Assessment

Glycoproteins A & B were subjected to side by side testing in HPLC/NQAD and HPLC/DMB methods as well as in HPAEC-PAD method. For HPLC/NQAD method, sialidase-A released NANA was analyzed using the chromatographic parameters and NQAD settings described in section 4.4. For HPLC/DMB method, analysis was carried out on Waters Alliance system equipped with fluorescence detector. An ultrasphere ODS column (Beckman) was used for the separation. The mobile phase for the isocratic separation of NANA and NGNA consisted of 78% water/21% methanol/0.3% acetonitrile. The column eluate was moni tored using fluorescent detector at 374 nm and 448 nm excitation and emission wavelengths, respectively. For the HPAEC-PAD method, sialidase-A released NANA was analyzed using 0.1 M sodium hydroxide and 0.1 M sodium hydroxide w/1M sodium acetate as mobile phases A & B, respectively. A linear gradient of 5% B to 18% B over 35 minutes was applied. Eluate was monitored using pulsed amperometric detector (PAD). NANA concentration obtained from HPLC/NQAD method was compared against the results obtained from HPLC/DMB and HPAEC-PAD methods to determine the comparability of HPLC/NQAD method to the two orthogonal methods.

RESULTS: Comparability results of HPLC/NQAD vs. HPAEC-PAD and HPLC/DMB are shown below in Tables 1 & 2, respectively. While orthogonal methods (HPAEC-PAD & HPLC/DMB) are being used for the sialic quantitation of glycoprotein-A, HPAEC-PAD method is the only method available for glycoprotein-B. Therefore, HPLC/NQAD method was only compared against HPAEC-PAD for glycoprotein-B. HPLC/NQAD results were comparable to the orthogonal methods for the tested samples.

TABLE 1

Comparison of HPLC/NQAD vs. HPAEC-PAD

| Sample ID | NANA content mol/mol HPLC/NQAD | NANA content mol/mol HPAEC-PAD | % RSD Between HPLC/NQAD & HPAEC-PAD |
|---|---|---|---|
| Glycoprotein A Lot # A1 | 13.67 | 12.96 | 4 |
| Glycoprotein A Lot # A2 | 13.59 | 12.48 | 6 |
| Glycoprotein A Lot # A3 | 13.28 | 12.82 | 2 |
| Glycoprotein A Lot # A4 | 13.26 | 12.52 | 4 |
| Glycoprotein A Lot # A5 | 13.25 | 12.86 | 2 |
| Glycoprotein A Lot # A6 | 12.50 | 11.48 | 6 |
| Glycoprotein A Lot # A7 | 13.48 | 12.46 | 5 |
| Glycoprotein A Lot # A8 | 13.64 | 12.54 | 6 |
| Glycoprotein A Lot # A9 | 12.71 | 11.82 | 5 |
| Glycoprotein B Lot # B1 | 21.1 | 22.3 | 4 |
| Glycoprotein B Lot # B2 | 25.5 | 23.3 | 6 |
| Glycoprotein B Lot # B3 | 22.5 | 22.4 | 0.3 |

TABLE 2

Comparison of HPLC/NQAD vs. HPLC/DMB

| Sample ID | NANA content mol/mol HPLC/NQAD | NANA content mol/mol HPLC/DMB | % RSD Between HPLC/NQAD & HPLC/DMB |
|---|---|---|---|
| Glycoprotein A Lot # A1 | 16.54 | 15.26 | 6 |
| Glycoprotein A Lot # A2 | 16.79 | 16.33 | 2 |
| Glycoprotein A Lot # A3 | 13.22 | 13.47 | 1 |
| Glycoprotein A Lot # A4 | 13.77 | 13.96 | 1 |
| Glycoprotein A Lot # A5 | 13.34 | 13.86 | 3 |

Example 6

6. Qualification of NANA Quantiation Assay w/ PolyGLYCOPLEX Amide Column

The short column method (w/5 cm PolyGLYCOPLEX amide column) described in section 4.4 was subjected to formal method qualification. Short HPLC/NQAD method (w/5 cm PolyGLYCOPLEX amide column) met all qualification criteria for accuracy, linearity and method precision (repeatability and intermediate precision). The LOD and LOQ of the method were determined to be 0.32 and 0.86 nmol/inj., respectively. Detailed results are shown in sections 6.1 through 6.4.

6.1 Accuracy Assessment of HPLC/NQAD Method

In order to assess the accuracy, spiking study was conducted in which known amounts of NANA at various concentrations were spiked into glycoprotein-A. The spiked and non-spiked samples were then subjected to HPLC/NQAD analysis subsequent to sialidase digestion. NANA concentrations obtained for the non-spiked samples were subtracted from spiked samples, which then were compared against the known amount of spiked NANA to determine the actual recoveries. To further verify the accuracy, Mass Spectrometric analysis was performed on HPLC/NQAD eluate of enzymatically digested Glycoprotein-A.

RESULTS: As illustrated in Table 3, results of spike & recovery experiments have demonstrated that the recoveries of NANA spiked into glycoprotein-A at various levels are within the 90-110% range. The TIC traces and corresponding Mass spectra indicated that the NANA peak obtained from HPLC/NQAD method was pure and no other interfering components co-eluted with NANA.

TABLE 3

Spike and Recovery results

| Sample | Spiked NANA (nmol/inj) | NANA Recovered (nmol/inj) | % Recovery |
|---|---|---|---|
| Glycoprotein-A (2 µl) | 5.9 | 5.8 | 98.9 |
| Glycoprotein-A (4 µl) | 10.8 | 10.8 | 100.3 |
| Glycoprotein-A (6 µl) | 14.9 | 14.4 | 96.3 |
| Glycoprotein-A (8 µl) | 18.5 | 19.8 | 107.3 |
| Glycoprotein-A (10 µl) | 21.6 | 21.5 | 99.8 |

6.2 Linear Dynamic Range Assessment

Linear dynamic range of the assay was determined by running sets of NANA standards at various concentrations. As illustrated in Table 4, the linear dynamic range of the assay has been determined to be in the range of 1-32 nmol/inj with a coefficient of determination $(R^2)=>0.99$. Corresponding linear regression plot is shown in FIG. 9.

TABLE 4

Linear Dynamic Range Assessment Results

| Concentration of standard (nmol/inj) | Concentration of standard (ng/inj) | NQAD Response [peak area (mV * sec)] | $R^2$ |
|---|---|---|---|
| 1.01 | 312.5 | 9.4 | 0.9998 |
| 2.02 | 625 | 20.5 | |
| 4.04 | 1250 | 47.7 | |
| 8.08 | 2500 | 101.2 | |
| 16.17 | 5000 | 219.7 | |
| 32.33 | 10000 | 446.7 | |

6.3 Assessment of Method Precision

The method precision, the closeness of agreement between a series of measurements obtained from multiple samples of the same sample type under the prescribed conditions, was assessed at two levels—repeatability and intermediate precision.

6.3.1 Repeatability

Repeatability or intra-assay precision is expressed under the same operating conditions over a short interval of time. To demonstrate repeatability of the method, released sialic acid (NANA) from glycoprotein-A was analyzed in 6 replicate injections. The relative standard deviation calculated from multiple injections was compared against the predicted performance target determined from Horwitz equation (Horwitz, 1982) presented below.

$$\% \ RSD < 2^{(2.5-0.5 \ log \ C)RSD}$$

Where C is the concentration of the analyte in the sample in mg/mL.

RESULTS: The % RSD of 0.96 determined from repeatability assessment was within the performance target of % RSD of <4 established based on Horwitz equation was fully satisfied. The precision of an analytical procedure that is usually expressed as standard deviation or % RSD of a series of measurements is shown in Table 5.

TABLE 5

Glycoprotein-A Repeatability results
Glycoprotein-A repeatability

| Glycoprotein-A | NANA (mol/mol) |
|---|---|
| Replicate 1 | 13.389 |
| Replicate 2 | 13.441 |
| Replicate 3 | 13.678 |
| Replicate 4 | 13.424 |
| Replicate 5 | 13.420 |
| Replicate 6 | 13.629 |
| Average | 13.497 |
| Standard Deviation | 0.13 |
| % RSD | <0.96 |

6.3.2 Intermediate Precision

Intermediate precision is expressed as variations within laboratories such as different days, different analysts, different equipment, etc. In order to assess the intermediate precision, analysis was carried out by two analysts on different days. The observed intermediate precisions were compared against the predicted performance target determined from the Horwitz equation.

RESULTS: Intermediate precision was established by analyzing glycoprotein-A on two different days and by two analysts. The % RSD of 0.95 is within the erformance target of % RSD≤6 established by Horwitz equation. The precision of an analytical procedure that is expressed as the variance, standard deviation or coefficient of variation of a series of measurements is shown in Tables 6.

TABLE 6

Intermediate precision results
Glycoprotein intermediate precision day 1 (Analysts 1 & 2)

| Glycoprotein-A | NANA (mol/mol) Analyst 1 (Day1) | NANA (mol/mol) Analyst 2 (Day1) | NANA (mol/mol) Analyst 1 (Day2) |
|---|---|---|---|
| Replicate 1 | 13.692 | 13.475 | 13.478 |
| Replicate 2 | 13.625 | 13.733 | 13.440 |
| Replicate 3 | 13.661 | 13.351 | 13.544 |
| Mean | 13.56 | | |
| STDEV | 0.13 | | |
| % RSD | 0.95 | | |

6.4 Assessment of LOD/LOQ

While LOD describes the lowest analyte concentration likely to be reliably distinguished from the noise, LOQ is the smallest concentration that can be reliably measured by the analytical method. A traditional and typical approach to estimate LOD and LOQ consists of measuring replicates (usually n=20) of a zero calibrator or blank sample and converting the response to nmol/injection using linear regression equation derived from the standard curve. For LOD and LOQ determination, 30 replicates of matrix blanks (water) and 10 replicates of lowest sialic acid standards (1 nanomole/injection) were analyzed. Standard curve constructed from concurrently analyzed sialic acid standards facilitate the conversion of responses to nmol/injection. LOD and LOQ were determined from the data generated from 30 replicate runs of blank and 10 replicate runs of lowest sialic acid standard (1.0 nmol/inj.). The raw data was converted to nmol/inj using linear regression equation. While mean+3.3 SD was used to determine the LOD, mean+10 SD was used to determine the LOQ. As shown in Table 7, the LOD and LOQ of the method, determined from 30 blank injections, were 0.32 and 0.86 nmol/inj., respectively. The average observed value of 0.99 nmol/inj determined from 10 injections of lowest sialic acid standard is well within the expected value of 1.0 nmol/inj., which verifies accuracy of the lowest standard. The % RSD between multiple values of lowest standard is 9%, which verifies the precision of the lowest standard.

TABLE 7

LOD/LOQ determination based on 30 blank injections verification based on 10 injection of the lowest (1 nanomole/inj.) sialic acid standard

| Blank Inj # | Cal Value (nmol/inj) | Lowest NANA Std Inj # | NANA (nmol/inj) |
|---|---|---|---|
| 1 | 0.41 | 1 | 0.88 |
| 2 | 0.20 | 2 | 0.96 |
| 3 | 0.07 | 3 | 0.85 |
| 4 | 0.11 | 4 | 1.06 |
| 5 | 0.08 | 5 | 0.95 |
| 6 | 0.03 | 6 | 0.93 |
| 7 | 0.03 | 7 | 1.12 |
| 8 | 0.04 | 8 | 1.10 |
| 9 | 0.03 | 9 | 1.05 |
| 10 | 0.08 | 10 | 0.99 |
| 11 | 0.03 | | |
| 12 | 0.04 | | |
| 13 | 0.02 | | |
| 14 | 0.04 | | |
| 15 | 0.04 | | |
| 16 | 0.04 | | |
| 17 | 0.04 | | |
| 18 | 0.02 | | |
| 19 | 0.02 | | |
| 20 | 0.02 | | |
| 21 | 0.02 | | |
| 22 | 0.05 | | |
| 23 | 0.02 | | |
| 24 | 0.01 | | |
| 25 | 0.01 | | |
| 26 | 0.02 | | |
| 27 | 0.02 | | |
| 28 | 0.02 | | |
| 29 | 0.06 | | |
| 30 | 0.26 | | |
| Avg. | 0.06 | | 0.99 |
| Std Dev | 0.08 | | 0.09 |
| % RSD | | | 9% |
| LOD | 0.32 | | |
| LOQ | 0.86 | | |

Discussion

Based on the summarized data in Table 1, we did not further pursue the RP-HPLC method to quantitate non-derivatized sialic acid. Despite the common use of RP-HPLC for the quantitation of DMB (1, 2-diamino-4, 5-methylenedioxybenzene) derivatized sialic acid, highly polar non-derivatized sialic acid could not be retained on RP-HPLC without some form of pre-derivatization. Table 1 also summarizes the positive and negative application of other modes of column chemistry (ion-pair chromatography, Ion- Exclusion chromatography, cation and anion exchange chromatography, and hydrophobic interaction chromatograph) for the quantitation of non-derivatized sialic acid.

Limited evaluation carried out to increase the hydrophobicity to improve the binding of non-derivatized sialic acid to RP-HPLC column through utilization of ion-pair reagents was not successful. As ion-pair chromatography was evaluated only with limited scope, the future researchers can explore this area by using various different anion and cation ion-pair reagents at various concentrations to improve the binding.

As NQAD detector is not compatible with high salt, AEX and CEX with salt gradients were not pursued. For the same reason, hydrophobic interaction chromatography was also opted out from the evaluation.

Both anion and cation exchange chromatography with pH gradient were evaluated without any successful outcome. Evaluation of mixed mode Ion Exclusion chromatography column is not promising due to the poor sensitivity associated with larger column dimension.

As shown in FIGS. 2 & 3, X-bridge and PolyGLYCOPLEX HILIC columns are suitable for retaining non-derivatized sialic acid. As PolyGLYCOPLEX amide column exhibited relatively better baseline than X-bridge column, PolyGLYCOPLEX amide column was selected for further optimization. With the use of PolyGLYCOPLEX amide column, acceptable peak symmetry was achieved under two elution conditions: (1) 10 cm column with acetonitrile as mobile phase A and 20% formic acid as mobile phase B (2) 5 cm column with acetonitrile as mobile phase A and 1% formic acid as mobile phase B. While the first option is better suited for situations in which the analytes have both NANA and NGNA present in them (FIG. 4), the second option is ideal if glycoproteins containing only NANA (FIG. 6).

The comparable peak response exhibited by centricon filtered and un-filtered samples (sialidase treated glycoprotein digest) suggest that matrix interference from the glycoprotein or other matrix components is not an issue. Therefore, centricon filtration applied to remove the protein and matrix components is not a required step.

As summarized in Tables 2 & 3, sialic acid quantitation results obtained from HPLC/NQAD are in good agreement with the orthogonal methods. The recovery of 95-105% (Table 4) obtained from spike and recovery (glycoprotein-A spiked with NANA at various levels) experiment as well as the comparable results of HPLC/NQAD method to the orthogonal methods (Tables 2 & 3) further support the accuracy of the method.

Linear range of HPLC/NQAD method is 1-32 nmol/inj with a coefficient of determination (R)=>0.99 (Table 5). The % RSDs of 0.96% and 0.95% (Tables 6 & 7) determined from repeatability (intra-assay precision) and intermediate precision were well within the performance target of ≤4% and ≤6% RSDs, respectively established from Horwitz equation.

There is no significant time saving from the chromatographic analysis times as the analysis times are comparable for HPLC/NQAD, HPAEC/PAD and HPLC/DMB with respective run times of 30 minutes, 31 minutes and 35 minutes. However, the HPLC/NQAD method provides cost benefit over HPLC/DMB method as the costly and time consuming dervatization step is eliminated.

From the scheduling perspective, removal of derivatization is beneficial. For example, the sample drying process in speed vac is expected to complete in approximately 2 hours. However, it often can vary from time to time and add additional uncertainty to the testing timeline. Although the sample preparation time and analysis time are comparable between HPLC/NQAD and HPAEC/PAD, HPLC/NQAD outperforms HPAEC/PAD in terms of reliability and ease of use.

CONCLUSION

As the sialic acid moiety of protein therapeutics influences the biological and physiochemical properties in addition to playing an important role in maintaining serum half-life, quantitation of sialic acid in glycoprotein is a required analytical step in characterizing bio-therapeutic proteins. The derivatization-free HPLC/NQAD method described herein is an efficient and reliable technique for the accurate quantitation of non-derivatized sialic acid in recombinant protein therapeutics. Enzymatically released sialic acid from protein therapeutics separated by PolyGLYCOPLEX HILIC column can be detected and quantitated using a nano quantity analyte detector (NQAD). While the accurate measurement of sialic acid content is critical for many therapeutic proteins, currently employed techniques such as HPAEC/PAD and HPLC/DMB face various issues. While the HPLC/DMB method requires tedious derivatization, the HPAEC/PAD method suffers issues such as electrode fouling and high maintenance costs. In addition to eliminating variability associated with derivatization, the HPLC/NQAD method has demonstrated linear dynamic range as well as excellent precision, repeatability, reliability, accuracy and ease of use with acceptable comparability to the commonly used HPAE-PAD and HPLC/DMB) methods.

REFERENCES

1. Byrne, B., Donohoe, G., & O'Kennedy, R. (2007). Sialic acids: carbohydrate moieties that influence the biological and physical properties of bio-pharmaceutical proteins and living cells. Drug Discovery Today 12(7/8): 319-326.
2. Hildenbrandt, G., & Aronson, N. (1979). Uptake of asialo-gycophorin by the perfused rat liver and isolated hepatocytes. Biochemica Et Biophysica Acta 587(3): 373-80.
3. Ganesa, C., Granda, B. W., & Mattaliano, R. J. (2003). Sialylation levels influence oligosaccharide quantitation: Analyzing response variability using high-pH anion-exchange chromatography and pulsed amperometric detection. Biopharm International 16(6): 44-48.
4. Hutchinson J P; Li J; Farrell W; Groeber E; Szucs R; Dicinoski G & Haddad P R. (2011). Comparison of the response of four aerosol detectors used with ultra high pressure liquid chromatography. Journal of Chromatography 1281(12): 1446-55.
5. Olsovská J; Kameník Z; Cajthaml T. (2009). Hyphenated ultra high-performance liquid chromatography-Nano Quantity Analyte Detector technique for determination of compounds with low UV absorption. Journal of Chromatography 1261(30): 5774-8.
6. Kimball, B., Arjo, W., Johnston, J. (2004). Single point calibration with non-linear detector: Carbohydrate analysis of conifer needles by hydrophobic interaction chromatography-evaporative light scattering detector. Journal of Liquid Chromatography & Related Technologies 27(12): 1835-1848.
7. Cintron, J & Risley, D. (2013). Hydrophilic interaction chromatography with aerosol-based detectors for polar compounds lacking UV chromophore in an intravenous formulation. Journal of Pharmaceutical and Biomedical Analysis 78-79:14-18.
8. Sharma, V. K., Glick, J., Vouros, P. (2012). Reversed-phase ion-pair liquid chromatography electro spray ionization tandem mass spectrometry for separation, sequencing and mapping of sites of base modification of isomeric oligonucleotide adducts using monolithic column. Journal of Chromatography A 1245 (6): 65-74.
9. Calhoun, A. R., King, A. D. (2007). The solubility of ethane in aqueous solutions of sodium 1-pentanesulfonate, sodium 1-hexanesulfonate, sodium 1-heptanesulfonate, and sodium 1-octanesulfonate at 25° C. Journal of Colloid and Interface Science 309 (2): 505-510.
10. Remsburg, J. W. (2007). Multiply charged cationic pairing agents for trace analysis of anionic species by electro spray ionization mass spectrometry. (Order No. 1447279, The University of Texas at Arlington). ProQuest Dissertations and Theses 77.
11. Isakau, H., Robert, M., & Shingel, K. (2009). A novel derivatization-free method of formaldehyde and propylene glycol determination in hydro gels by liquid chromatography with refractometric detection. Journal of Pharmaceutical and Biomedical Analysis 49(3): 594-600.
12. Mori, M., Taoda, H., Itabashi, H., Ikedo, M., & Tanaka, K. (2006). Use of combined ion-exclusion and cation exchange chromatography to study photooxidation of ionic nitrogen compounds on a titanium dioxide photo catalyst. ACTA CHROMATOGRAPHICA 1 (16): 28-37.
13. Horwitz, W. 1982. Evaluation of Analytical Methods Used for Regulation of Foods and Drugs. *Analytical Chemistry* 54:67-76.
14. Zauner, G., Deelder, M., & Wuhrer, M. (2011). A recent advance in hydrophilic interaction liquid chromatography (HILIC) for structural glycomics. Electrophoresis. 32(24): 3456-3466.
15. Ikegami, T., Tomomatsu, K., Takubo, H., Horie, K., Tanaka, N. (2008). Separation efficiencies in hydrophilic interaction chromatography. J. Chromatography 1184(1-2): 474-503.
16. Duy, S., Besteiro, S., Berry, L., Perigaud, C., Bressolle, F., Vial, H. J., Lefebvre-Tournier, I. (2012). A quantitative liquid chromatography tandem mass spectrometry method for metabolomic analysis of *Plasmodium falciparum* lipid related metabolites. Analytica Chemica Acta 739(20): 47-56.
17. Lin, S. L., Inoue, S., & Inoue, Y. (2000). Acid-base properties of the reaction product of sialic acid with flurogenic reagent, 1-2-diamino-4.5-methylethylene dioxybenzene (DMB) Carbohydrate Research 329(2): 447-451.
18. Horwitz, W. (1982). Evaluation of Analytical Methods Used for Regulation of Foods and Drugs. Analytical Chemistry 54 (1): 67-76.
19. Siskos, P A. & Spyridk, M H. (1999). Determination of sialic acids in biological fluids using reversed-phase ion-pair high-performance liquid chromatography. J. Chromatogr B Biomed Sci Appl 724(2): 205-12.

What is claimed is:

1. A method of determining sialic acid moiety on a recombinant glycoprotein, the method comprising digesting the recombinant glycoprotein with a sialidase to liberate sialic acid, loading the sialidase-digested recombinant glycoprotein onto a hydrophilic interaction chromatography (HILIC) column, eluting the liberated sialic acid with acetonitrile as mobile phase A and either 20% formic acid or 1% formic acid as mobile phase B, and quantitating the sialic acid using condensation nucleation light scattering detection.

2. The method of claim 1, wherein the condensation nucleation light scattering detection uses a Nano Quantity Analyte Detector (NQAD).

3. The method of claim 1, wherein the recombinant glycoprotein is an antibody, a fusion protein, a hormone, or a cytokine.

4. The method of claim 1, wherein the sialic acid is N-acetylneuraminic acid and/or N-glycolylneuramic acid.

5. The method of claim 4, wherein the amount of N-acetylneuraminic acid and/or N-glycolylneuramic acid is determined.

6. The method of claim 4, wherein the ratio of N-acetylneuraminic acid to N-glycolylneuramic acid is determined.

7. A method of determining glycan moiety on a recombinant glycoprotein, the method comprising digesting the recombinant glycoprotein with a glycosidase to liberate glycan, loading the sialidase-digested recombinant glycoprotein onto a hydrophilic interaction chromatography (HILIC) column, eluting the liberated sialic acid with acetonitrile as mobile phase A and either 20% formic acid or 1% formic acid as mobile phase B, and quantitating the glycan using condensation nucleation light scattering detection.

8. The method of claim 7, wherein the condensation nucleation light scattering detection uses a Nano Quantity Analyte Detector (NQAD).

9. The method of claim 7, wherein the recombinant glycoprotein is an antibody, a fusion protein, a hormone, or a cytokine.

10. The method of claim 7, wherein the glycan moiety is one or more of sialic acid moiety, terminal galactose, N-linked glycans, and O-linked glycans.

11. The method of claim 10, wherein the amount of glycan moiety is determined.

12. A method of determining sialic acid moiety on etanercept, the method comprising digesting the etanercept with a sialidase to liberate sialic acid, loading the sialidase-digested etanercept onto a hydrophilic interaction chromatography (HILIC) column, eluting the liberated sialic acid with acetonitrile as mobile phase A and either 20% formic acid or 1% formic acid as mobile phase B, and quantitating the sialic acid using condensation nucleation light scattering detection.

13. The method of claim 12, wherein the sialic acid is N-acetylneuraminic acid and/or N-glycolylneuramic acid.

14. The method of claim 13, wherein the amount of N-acetylneuraminic acid and/or N-glycolylneuramic acid is determined.

15. The method of claim 13, wherein the ratio of N-acetylneuraminic acid to N-glycolylneuramic acid is determined.

* * * * *